(12) United States Patent
Qiu et al.

(10) Patent No.: US 6,774,115 B1
(45) Date of Patent: Aug. 10, 2004

(54) 6-O-SUBSTITUTED BICYCLIC KETOLIDES

(75) Inventors: Yao-Ling Qiu, Andover, MA (US); Ly Tam Phan, Malden, MA (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 10/454,865

(22) Filed: Jun. 5, 2003

(51) Int. Cl.⁷ .......................... A61K 31/70; C07H 17/08
(52) U.S. Cl. ..................... 514/29; 536/7.2; 536/7.3; 536/7.4
(58) Field of Search .................... 536/7.2, 7.3, 7.4; 514/29

(56) References Cited

U.S. PATENT DOCUMENTS

| | | | |
|---|---|---|---|
| 5,866,549 A | 2/1999 | Or et al. | 514/29 |
| 6,124,269 A | 9/2000 | Phan et al. | 514/29 |
| 6,399,582 B1 | 6/2002 | Hlasta et al. | 514/29 |

FOREIGN PATENT DOCUMENTS

| | | | | |
|---|---|---|---|---|
| WO | WO 97/042205 A1 | 11/1997 | | C07H/17/08 |
| WO | WO 02/016380 A1 | 2/2002 | | C07H/17/08 |
| WO | WO 02/050091 A1 | 6/2002 | | C07H/17/08 |
| WO | WO 02/050092 A1 | 6/2002 | | C07H/17/08 |
| WO | WO 03/004509 A2 | 1/2003 | | C07H/17/08 |
| WO | WO 03/024986 A1 | 3/2003 | | C07H/17/08 |

OTHER PUBLICATIONS

Anhydrolide Macrolides. 1. Sythesis and Antibacterial Activity of 2,3–Anhydro–6–O–methyl 11,12–Carbamate Erythromycin A Analogs, Elliott et al, J. Med. Chem. 1998, 41, 1651–1659.

Anhydrolide Macrolides. 2. Sythesis and Antibacterial Activity of 2,3–Anhydro–6–O–methyl 11,12–Carbazate Erythromycin A Analogs, Griesgraber et al, J. Med. Chem. 1998, 41, 1660–1670.

*Primary Examiner*—Elli Peselev
(74) *Attorney, Agent, or Firm*—Jason D. Ferrone

(57) ABSTRACT

The present invention discloses compounds of formula I, or pharmaceutically acceptable salts, esters, or prodrugs thereof:

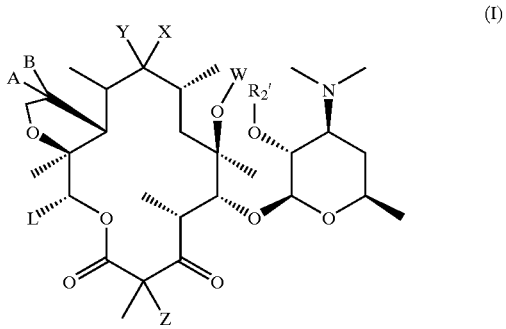

(I)

which exhibit antibacterial properties. The present invention further relates to pharmaceutical compositions comprising the aforementioned compounds for administration to a subject in need of antibiotic treatment. The invention also relates to methods of treating a bacterial infection in a subject by administering a pharmaceutical composition comprising the compounds of the present invention. The invention further includes process by which to make the compounds of the present invention.

8 Claims, No Drawings

6-O-SUBSTITUTED BICYCLIC KETOLIDES

REFERENCE TO RELATED APPLICATIONS

This application is related to commonly assigned U.S. patent application Ser. Nos. 10/455,219, 10/455,648 and 10/455,001, filed on even date herewith.

TECHNICAL FIELD

The present invention relates to novel semisynthetic macrolides having antibacterial activity and which are useful in the treatment and prevention of bacterial infections. More particularly, the invention relates to 11,12-cyclized erythromycin derivatives, compositions containing such compounds and methods for using the same, as well as processes for making such compounds.

BACKGROUND OF THE INVENTION

Erythromycins A through D, represented by formula (E) as illustrated below,

| Erythromycin | $R^a$ | $R^b$ |
|---|---|---|
| A | —OH | —$CH_3$ |
| B | —H | —$CH_3$ |
| C | —OH | —H |
| D | —H | —H | are well-known and potent antibacterial agents, used widely to treat and prevent bacterial infection. As with other antibacterials, however, bacterial strains having resistance or insufficient susceptibility to erythromycin have been identified. Also, erythromycin A has only weak activity against Gram-negative bacteria. Therefore, there is a continuing need to identify new erythromycin derivative compounds which possess improved antibacterial activity, which have less potential for developing resistance, which possess the desired Gram-negative activity, or which possess unexpected selectivity against target microorganisms. Consequently, numerous investigators have prepared chemical derivatives of erythromycin in an attempt to obtain analogs having modified or improved profiles of antibiotic activity.

Kashimura et al. have disclosed 6-O-methylerythromycin derivatives having a tricyclic basic nuclear structure in European Application 559896, published Nov. 11, 1991.

Also, Asaka et al. have disclosed 5-O-desoaminylerythronolide derivatives containing a tricyclic carbamate structure in PCT Application WO 93/21200, published Apr. 22, 1992.

Recently erythromycin derivatives containing a variety of substituents at the 6-O position have been disclosed in U.S. Pat. Nos. 5,866,549, 6,075,011 and 6,420,555 B1 as well as PCT Applications WO 00/78773 and WO 03/024986. Furthermore, Ma et. al. have described erythromycin derivatives with aryl groups tethered to the C-6 position in *J. Med Chem.*, 44, pp 4137–4156 (2001).

More recently, erythromycin derivatives containing a lactone moiety at the C11–C12 position have been disclosed in PCT Application WO 02/16380, published Feb. 28, 2002 as well as WO 02/50091 and WO 02/50092, both published Jun. 27, 2002 and WO 03/024986, which published Mar. 27, 2003.

SUMMARY OF THE INVENTION

The present invention provides a novel class of C11–C12 cyclized erythromycin compounds that possess antibacterial activity.

In one aspect of the present invention there are disclosed novel bicyclic erythromycin compounds represented by formula I as illustrated below:

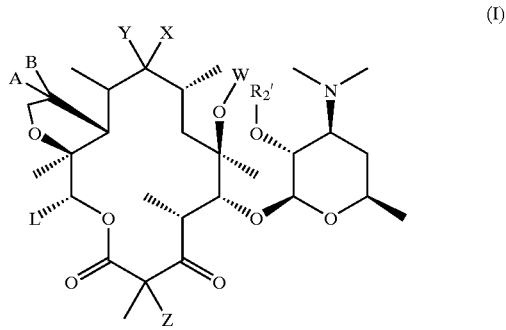

(I)

as well as the pharmaceutically acceptable salts, esters and prodrugs thereof.

In formula I:

A is selected from:
- (a) —OH;
- (b) —$OR_p$, where $R_p$ is a hydroxy protecting group;
- (c) —$R_1$, where $R_1$ is selected from:
  1. aryl;
  2. substituted aryl;
  3. heteroaryl; and
  4. substituted heteroaryl;
- (d) —$OR_1$, where $R_1$ is as previously defined;
- (e) —$R_2$, where $R_2$ is selected from:
  1. hydrogen;
  2. halogen;
  3. $C_1$–$C_6$ alkyl containing 0, 1, 2, or 3 heteroatoms selected from O, S and N, optionally substituted with one or more substituents selected from halogen, cyano, oxo, aryl, substituted aryl, heteroaryl and substituted heteroaryl;
  4. $C_2$–$C_6$ alkenyl containing 0, 1, 2, or 3 heteroatoms selected from O, S and N, optionally substituted with one or more substituents selected from halogen, cyano, oxo, aryl, substituted aryl, heteroaryl and substituted heteroaryl; and
  5. $C_2$–$C_6$ alkynyl containing 0, 1, 2, or 3 heteroatoms selected from O, S and N, optionally substituted with one or more substituents selected from halogen, cyano, oxo, aryl, substituted aryl, heteroaryl and substituted heteroaryl;

(f) —$OR_2$, where $R_2$ is previously defined;

(g) —$S(O)_nR_{11}$, where n=0, 1 or 2, and $R_{11}$ is selected from hydrogen, $R_1$ and $R_2$, where $R_1$ and $R_2$ are as previously defined;

(h) —$OC(O)R_{11}$, where $R_{11}$ is as previously defined;

(i) —$C(O)R_{11}$, where $R_{11}$ is as previously defined;

(j) —$C(O)NHR_{11}$, where $R_{11}$ is as previously defined;

(k) —$OC(O)NHR_{11}$, where $R_{11}$ is as previously defined;

(l) —$NHC(O)R_{11}$, where $R_{11}$ is as previously defined;

(m) —$NHC(O)NHR_{11}$, where $R_{11}$ is as previously defined;

(n) —$NHS(O)_nR_{11}$, where n and $R_{11}$ are as previously defined;

(o) —$NR_{14}R_{15}$, where $R_{14}$ and $R_{15}$ are each independently $R_{11}$, where $R_{11}$ is as previously defined; and (p) —$NHR_3$, where $R_3$ is an amino protecting group;

B is selected from:
(a) hydrogen;
(b) deuterium;
(c) —CN;
(d) —$NO_2$;
(e) halogen;
(f) —OH;
(g) —$R_1$, where $R_1$ is as previously defined;
(h) —$R_2$, where $R_2$ is as previously defined; and
(i) —$OR_p$, where $R_p$ is as previously defined;

provided that when B is halogen, —$NO_2$, —OH or $OR_p$, A is $R_1$ or $R_2$;

or, alternatively, A and B taken together with the carbon atom to which they are attached are selected from:
(a) C=O;
(b) $C(OR_2)_2$, where $R_2$ is as previously defined;
(c) $C(SR_2)_2$, where $R_2$ is as previously defined;
(d) $C(OR_{12})(OR_{13})$, where $R_{12}$ and $R_{13}$ taken together are —$(CH_2)_m$—, and where m is 2 or 3;
(e) $C(SR_{12})(SR_{13})$, where $R_{12}$ and $R_{13}$ taken together are —$(CH_2)_m$—, where m is as previously defined;
(f) C=$CR_{11}R_{14}$, where $R_{11}$ and $R_{14}$ are as previously defined;
(g) C=N—O—$R_{11}$, where $R_{11}$ is as previously defined;
(h) C=$NNHR_{11}$, where $R_{11}$ is as previously defined;
(i) C=$NNHC(O)R_{11}$, where $R_{11}$ is as previously defined;
(j) C=NN=$CR_{11}R_{14}$, where $R_{11}$ and $R_{14}$ are as previously defined;
(k) C=$NNHC(O)NHR_{11}$, where $R_{11}$ is as previously defined;
(l) C=$NNHS(O)_nR_{11}$, where n and $R_{11}$ are as previously defined;
(m) C=$NNHR_3$, where $R_3$ is as previously defined; and
(n) C=$NR_{11}$, where $R_{11}$ is as previously defined;

one of X and Y is hydrogen and the other is selected from:
(a) hydrogen;
(b) deuterium;
(c) —OH;
(d) —$OR_p$, where $R_p$ is as previously defined; and
(e) —$NR_4R_5$, where $R_4$ and $R_5$ are each independently selected from:
1. hydrogen; and
2. $C_1$–$C_{12}$ alkyl, optionally substituted with one or more substituents selected from halogen, cyano, aryl, substituted aryl, heteroaryl and substituted heteroaryl; or
$R_4$ and $R_5$, taken together with the nitrogen atom to which they are attached form a 3–10 membered heteroalkyl ring containing 0–2 additional hetero atoms selected from the group consisting of O, S and N; or alternatively, X and Y taken together with the carbon atom to which they are attached are selected from:
(a) C=O;
(b) C=$NR_{11}$, where $R_{11}$ is as previously defined;
(c) C=$NC(O)R_{11}$, where $R_{11}$ is as previously defined;
(d) C=N—$OR_6$, where $R_6$ is selected from:
1. hydrogen;
2. —$CH_2O(CH_2)_2OCH_3$;
3. —$CH_2O(CH_2O)_nCH_3$, where n is as previously defined;
4. —$C_1$–$C_{12}$ alkyl, optionally substituted with one or more substituents selected from halogen, cyano, aryl, substituted aryl, heteroaryl and substituted heteroaryl;
5. $C_3$–$C_{12}$ cycloalkyl;
6. C(O)—$C_1$–$C_{12}$ alkyl;
7. C(O)—$C_3$–$C_{12}$ cycloalkyl;
8. C(O)—$R_1$, where $R_1$ is as previously defined; and
9. —$Si(R_a)(R_b)(R_c)$, wherein $R_a$, $R_b$ and $R_c$ are each independently selected from $C_1$–$C_{12}$ alkyl, aryl and substituted aryl; and
(e) C=N—O—$C(R_7)(R_8)$—O—$R_6$, where $R_6$ is as previously defined, provided that $R_6$ is not C(O)—$C_1$–$C_{12}$ alkyl, C(O)—$C_3$–$C_{12}$ cycloalkyl, or C(O)—$R_1$; and $R_7$ and $R_8$ taken together with the carbon atom to which they are attached form a $C_3$–$C_{12}$ cycloalkyl group or each is independently selected from:
1. hydrogen; and
2. $C_1$–$C_{12}$ alkyl;

L is selected from:
(a) —$CH(OH)CH_3$;
(b) $C_1$–$C_6$ alkyl, optionally substituted with one or more substituents selected from halogen, cyano, aryl, substituted aryl, heteroaryl, and substituted heteroaryl;
(c) $C_2$–$C_6$ alkenyl, optionally substituted with one or more substituents selected from halogen, cyano, aryl, substituted aryl, heteroaryl, and substituted heteroaryl; and
(d) $C_2$–$C_6$ alkynyl, optionally substituted with one or more substituents selected from halogen, cyano, aryl, substituted aryl, heteroaryl, and substituted heteroaryl;

W is selected from:
(a) $C_2$–$C_6$ alkyl containing 0, 1, 2, or 3 heteroatoms selected from O, S and N, optionally substituted with one or more substituents selected from halogen, cyano, oxo, aryl, substituted aryl, heteroaryl, and substituted heteroaryl;
(b) $C_2$–$C_6$ alkenyl containing 0, 1, 2, or 3 heteroatoms selected from O, S and N, optionally substituted with one or more substituents selected from halogen, cyano, oxo, aryl, substituted aryl, heteroaryl, and substituted heteroaryl; and
(c) $C_2$–$C_6$ alkynyl containing 0, 1, 2, or 3 heteroatoms selected from O, S and N, optionally substituted with one or more substituents selected from halogen, cyano, oxo, aryl, substituted aryl, heteroaryl, and substituted heteroaryl;

Z is selected from:
(a) hydrogen;
(b) halogen; and
(c) $C_1$–$C_6$alkyl, optionally substituted with one or more subtstitnients selected from halogen, cyano, aryl, substituted aryl, heteroaryl and substituted heteroaryl; and $R_2'$ is hydrogen or $R_p$, where $R_p$ is as previously defined.

In another aspect of the present invention there are disclosed pharmaceutical compositions comprising a therapeutically effective amount of a compound of the invention in combination with a pharmaceutically acceptable carrier, and treatment of antibacterial infections with such compositions. Suitable carriers and methods of formulation are also disclosed. The compounds and compositions of the present invention have antibacterial activity.

In a further aspect of the present invention there are provided processes for the preparation of 11, 12-cyclized erythromycin derivatives of formula (I).

DETAILED DESCRIPTION OF THE INVENTION

A first embodiment of the present invention includes compounds represented by formula I, as illustrated above, as well as the pharmaceutically acceptable salts, esters and prodrugs thereof.

A preferred group of compounds of the present invention are those represented by formula I wherein L is ethyl and A, B, W, X, Y, Z and $R_2'$ are as previously defined.

Representative compounds of the invention are those selected from:

Compound of formula I: A and B taken together with the carbon atom to which they are attached are C=$CH_2$, L is $CH_2CH_3$, W is $CH_2CH$=$CH_2$, X and Y taken together with the carbon atom to which they are attached are C=O, Z is H, and $R_2'$ is H;

Compound of formula I: A and B taken together with the carbon atom to which they are attached are C=$CH_2$, L is $CH_2CH_3$, W is $CH_2CH$=CH-(3-quinolyl), X and Y taken together with the carbon atom to which they are attached are C=O, Z is H, and $R_2'$ is H;

Compound of formula I: A and B taken together with the carbon atom to which they are attached are C=$CH_2$, L is $CH_2CH_3$, W is $CH_2CH(O)$, X and Y taken together with the carbon atom to which they are attached are C=O, Z is H, and $R_2'$ is H;

Compound of formula I: A and B taken together with the carbon atom to which they are attached are C=$CH_2$, L is $CH_2CH_3$, W is $CH_2C$≡CH, X and Y taken together with the carbon atom to which they are attached are C=O, Z is H, and $R_2'$ is H;

Compound of formula I: A and B taken together with the carbon atom to which they are attached are C=$CH_2$, L is $CH_2CH_3$, W is $CH_2C$≡C-(3-quinolyl), X and Y taken together with the carbon atom to which they are attached are C=O, Z is H, and $R_2'$ is H;

Compound of formula I: A and B taken together with the carbon atom to which they are attached are C=$CH_2$, L is $CH_2CH_3$, W is $CH_2CH_2NHCH_2$-(4-chlorophenyl), X and Y taken together with the carbon atom to which they are attached are C=O, Z is H, and $R_2'$ is H;

Compound of formula I: A and B taken together with the carbon atom to which they are attached are C=$CH_2$, L is $CH_2CH_3$, W is $CH_2C$≡CH, X and Y taken together with the carbon atom to which they are attached are C=O, Z is F, and $R_2'$ is H;

Compound of formula I: A and B taken together with the carbon atom to which they are attached are C=$CH_2$, L is $CH_2CH_3$, W is $CH_2C$≡C-(3-quinolyl), X and Y taken together with the carbon atom to which they are attached are C=O, Z is F, and $R_2'$ is H;

Compound of formula I: A and B taken together with the carbon atom to which they are attached are C=$CH_2$, L is $CH_2CH_3$, W is $CH_2CH_2NCH_3CH_2$-phenyl, X and Y taken together with the carbon atom to which they are attached are C=O, Z is H, and $R_2'$ is H;

Compound of formula I: A and B taken together with the carbon atom to which they are attached are C=$CH_2$, L is $CH_2CH_3$, W is $CH_2CH_2NCH_3CH_2$-(2-pyridyl), X and Y taken together with the carbon atom to which they are attached are C=O, Z is H, and $R_2'$ is H;

Compound of formula I: A and B taken together with the carbon atom to which they are attached are C=$CH_2$, L is $CH_2CH_3$, W is $CH_2CH_2NCH_3CH_2$-(3-pyridyl), X and Y taken together with the carbon atom to which they are attached are C=O, Z is H, and $R_2'$ is H;

Compound of formula I: A and B taken together with the carbon atom to which they are attached are C=$CH_2$, L is $CH_2CH_3$, W is $CH_2CH_2NCH_3CH_2$-(3-quinolyl), X and Y taken together with the carbon atom to which they are attached are C=O, Z is H, and $R_2'$ is H;

Compound of formula I: A and B taken together with the carbon atom to which they are attached are C=$CH_2$, L is $CH_2CH_3$, W is $CH_2CH_2NCH_3CH_2$-(2-pyridyl), X and Y taken together with the carbon atom to which they are attached are C=O, Z is F, and $R_2'$ is H;

Compound of formula I: A and B taken together with the carbon atom to which they are attached are C=$CH_2$, L is $CH_2CH_3$, W is $CH_2CH_2NCH_3CH_2$-(3quinolyl), X and Y taken together with the carbon atom to which they are attached are C=O, Z is F, and $R_2'$ is H;

Compound of formula I: A and B taken together with the carbon atom to which they are attached are C=$CH_2$, L is $CH_2CH_3$, W is $CH_2CH$=CH-phenyl, X and Y taken together with the carbon atom to which they are attached are C=O, Z is H, and $R_2'$ is H;

Compound of formula I: A and B taken together with the carbon atom to which they are attached are C=$CH_2$, L is $CH_2CH_3$, W is $CH_2CH$=CH-(2-pyridyl), X and Y taken together with the carbon atom to which they are attached are C=O, Z is H, and $R_2'$ is H;

Compound of formula I: A and B taken together with the carbon atom to which they are attached are C=$CH_2$, L is $CH_2CH_3$, W is $CH_2CH$=CH-(3-pyridyl), X and Y taken together with the carbon atom to which they are attached are C=O, Z is H, and $R_2'$ is H;

Compound of formula I: A and B taken together with the carbon atom to which they are attached are C=$CH_2$, L is $CH_2CH_3$, W is $CH_2CH$=CH-(3-(5-cyano)pyridyl), X and Y taken together with the carbon atom to which they are attached are C=O, Z is H, and $R_2'$ is H;

Compound of formula I: A and B taken together with the carbon atom to which they are attached are C=$CH_2$, L is $CH_2CH_3$, W is $CH_2CH$=CH-(6-(aminocarbonyl)-3-quinolyl), X and Y taken together with the carbon atom to which they are attached are C=O, Z is H, and $R_2'$ is H;

Compound of formula I: A and B taken together with the carbon atom to which they are attached are C=$CH_2$, L is $CH_2CH_3$, W is $CH_2CH$=CH-(3quinolyl), X and Y taken together with the carbon atom to which they are attached are C=O, Z is F, and $R_2'$ is H;

Compound of formula I: A and B taken together with the carbon atom to which they are attached are C=$CH_2$, L is CH$_2$CH$_3$, W is CH$_2$CH=CH-(3-pyridyl), X and Y taken together with the carbon atom to which they are attached are C=O, Z is F, and R$_2$' is H;

Compound of formula I: A and B taken together with the carbon atom to which they are attached are C=CH$_2$, L is CH$_2$CH$_3$, W is CH$_2$C≡C-phenyl), X and Y taken together with the carbon atom to which they are attached are C=O, Z is H, and R$_2$' is H;

Compound of formula I: A and B taken together with the carbon atom to which they are attached are C=CH$_2$, L is CH$_2$CH$_3$, W is CH$_2$C≡C-(2-pyridyl), X and Y taken together with the carbon atom to which they are attached are C=O, Z is H, and R$_2$' is H;

Compound of formula I: A and B taken together with the carbon atom to which they are attached are C=CH$_2$, L is CH$_2$CH$_3$, W is CH$_2$C≡C-(3-pyridyl), X and Y taken together with the carbon atom to which they are attached are C=O, Z is H, and R$_2$' is H;

Compound of formula I: A and B taken together with the carbon atom to which they are attached are C=CH$_2$, L is CH$_2$CH$_3$, W is CH$_2$C≡C-(3-(5-cyano)pyridyl), X and Y taken together with the carbon atom to which they are attached are C=O, Z is H, and R$_2$' is H;

Compound of formula I: A and B taken together with the carbon atom to which they are attached are C=CH$_2$, L is CH$_2$CH$_3$, W is CH$_2$C≡C-(5-(2-pyridyl)-2-thienyl), X and Y taken together with the carbon atom to which they are attached are C=O, Z is H, and R$_2$' is H;

Compound of formula I: A and B taken together with the carbon atom to which they are attached are C=CH$_2$, L is CH$_2$CH$_3$, W is CH$_2$C≡C-(5-(3-pyridinyl)-2-pyrrolyl), X and Y taken together with the carbon atom to which they are attached are C=O, Z is H, and R$_2$' is H;

Compound of formula I: A and B taken together with the carbon atom to which they are attached are C=CH$_2$, L is CH$_2$CH$_3$, W is CH$_2$C≡C-(2-pyrimidyl)-2-thienyl), X and Y taken together with the carbon atom to which they are attached are C=O, Z is H, and R$_2$' is H;

Compound of formula I: A and B taken together with the carbon atom to which they are attached are C=CH$_2$, L is CH$_2$CH$_3$, W is CH$_2$C≡C-(5-(2-pyrazinyl)-2-pyrrolyl), X and Y taken together with the carbon atom to which they are attached are C=O, Z is H, and R$_2$' is H;

Compound of formula I: A and B taken together with the carbon atom to which they are attached are C=CH$_2$, L is CH$_2$CH$_3$, W is CH$_2$C≡C-(6-quinolyl), X and Y taken together with the carbon atom to which they are attached are C=O, Z is H, and R$_2$' is H;

Compound of formula I: A and B taken together with the carbon atom to which they are attached are C=CH$_2$, L is CH$_2$CH$_3$, W is CH$_2$C≡C-phenyl, X and Y taken together with the carbon atom to which they are attached are C=O, Z is F, and R$_2$' is H;

Compound of formula I: A and B taken together with the carbon atom to which they are attached are C=CH$_2$, L is CH$_2$CH$_3$, W is CH$_2$C≡C-(2-pyridyl), X and Y taken together with the carbon atom to which they are attached are C=O, Z is F, and R$_2$' is H;

Compound of formula I: A and B taken together with the carbon atom to which they are attached are C=CH$_2$, L is CH$_2$CH$_3$, W is CH$_2$C≡C-(3-pyridyl), X and Y taken together with the carbon atom to which they are attached are C=O, Z is F, and R$_2$' is H;

Compound of formula I: A and B taken together with the carbon atom to which they are attached are C=CH$_2$, L is CH$_2$CH$_3$, W is CH$_2$C≡C-(3-(5-cyano)pyridyl), X and Y taken together with the carbon atom to which they are attached are C=O, Z is F, and R$_2$' is H;

Compound of formula I: A and B taken together with the carbon atom to which they are attached are C=CH$_2$, L is CH$_2$CH$_3$, W is CH$_2$C≡C-(5-(2-pyridyl)-2-thienyl), X and Y taken together with the carbon atom to which they are attached are C=O, Z is F, and R$_2$' is H;

Compound of formula I: A and B taken together with the carbon atom to which they are attached are C=CH$_2$, L is CH$_2$CH$_3$, W is CH$_2$C≡C-(5-(2-pyrimidyl)-2-thienyl), X and Y taken together with the carbon atom to which they are attached are C=O, Z is F, and R$_2$' is H;

Compound of formula I: A and B taken together with the carbon atom to which they are attached are C=CH$_2$, L is CH$_2$CH$_3$, W is CH$_2$C≡C-(5-(2-pyridinyl)-2-pyrrolyl), X and Y taken together with the carbon atom to which they are attached are C=O, Z is F, and R$_2$' is H; and Compound of formula I: A and B taken together with the carbon atom to which they are attached are C=CH$_2$, L is CH$_2$CH$_3$, W is CH$_2$C≡C-(5-(2-pyrazinyl)-2-pyrrolyl), X and Y taken together with the carbon atom to which they are attached are C=O, Z is F, and R$_2$' is H.

Definitions

Listed below are definitions of various terms used to describe this invention. These definitions apply to the terms as they are used throughout this specification and claims, unless otherwise limited in specific instances, either individually or as part of a larger group.

The terms "$C_1$–$C_3$ alkyl," "$C_1$–$C_6$ alkyl," or "$C_1$–$C_{12}$ alkyl," as used herein, refer to saturated, straight- or branched-chain hydrocarbon radicals containing between one and three, one and twelve, or one and six carbon atoms, respectively. Examples of $C_1$–$C_3$ alkyl radicals include methyl, ethyl, propyl and isopropyl radicals; examples of $C_1$–$C_6$ alkyl radicals include, but are not limited to, methyl, ethyl, propyl, isopropyl, n-butyl, tert-butyl, neopentyl and n-hexyl radicals; and examples of $C_1$–$C_{12}$ alkyl radicals include, but are not limited to, ethyl, propyl, isopropyl, n-hexyl, octyl, decyl, dodecyl radicals.

The term "substituted alkyl," as used herein, refers to a "$C_2$–$C_{12}$ alkyl" or "$C_1$–$C_6$ alkyl" group as previously defined, substituted by independent replacement or one, two, or three of the hydrogen atoms thereon with substituents including, but not limited to, —F, —Cl, —Br, —I, —OH, protected hydroxy, —NO$_2$, —CN, —C$_1$–C$_{12}$-alkyl optionally substituted with halogen, C$_2$–C$_{12}$-alkenyl optionally substituted with halogen, —C$_2$–C$_{12}$-alkynyl optionally substituted with halogen, —NH$_2$, protected amino, —NH—C$_1$–C$_{12}$-alkyl, —NH—C$_2$–C$_{12}$-alkenyl —NH—C$_2$–C$_{12}$-alkenyl, —NH—C$_3$–C$_{12}$-cycloalkyl, —NH-aryl, —NH-heteroaryl, —NH-heterocycloalkyl, -dialkylamino, -diarylamino, -diheteroarylamino, —O—C$_1$–C$_{12}$-alkyl, —O—C$_2$–C$_{12}$-alkenyl, —O—C$_2$–C$_{12}$-alkenyl, —O—C$_3$–C$_{12}$-cycloalkyl, —O-aryl, —O-heteroaryl, —O-heterocycloalkyl, —C(O)—C$_1$–C$_{12}$-alkyl, —C(O)—C$_2$–C$_{12}$-alkenyl, —C(O)—C$_2$–C$_{12}$-alkenyl, —C(O)—C$_3$–C$_{12}$-cycloalkyl, —C(O)-aryl, —C(O)-heteroaryl, —C(O)-heterocycloalkyl, —CONH$_2$, —CONH—C$_1$–C$_{12}$-alkyl, —CONH—C$_2$–C$_{12}$-alkenyl, —CONH—C$_2$–C$_{12}$-alkenyl, —CONH—C$_3$–C$_{12}$-cycloalkyl, —CONH-aryl, —CONH-heteroaryl, —CONH-heterocycloalkyl, —OCO$_2$—C$_1$–C$_{12}$-alkyl, —OCO$_2$—C$_2$–C$_{12}$-alkenyl, —OCO$_2$—C$_2$–C$_{12}$-alkenyl, —OCO$_2$—C$_3$–C$_{12}$-cycloalkyl, —OCO$_2$-aryl, —OCO$_2$-heteroaryl, —OCO$_2$-heterocycloalkyl, —OCONH$_2$, —OCONH—C$_1$–C$_{12}$-alkyl, —OCONH—C$_2$–C$_{12}$-alkenyl, —OCONH—C$_2$–C$_{12}$-alkenyl, —OCONH—C$_3$–C$_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkenyl, —NHC(O)—$C_3$–$C_{12}$-cycloalkyl, —NHC(O)-aryl, —NHC(O)-heteroaryl, —NHC(O)-heterocycloalkyl, —NHCO$_2$—$C_1$–$C_{12}$-alkyl, —NHCO$_2$—$C_2$–$C_{12}$-alkenyl, —NHCO$_2$—$C_2$–$C_{12}$-alkenyl, —NHCO$_2$—$C_3$–$C_{12}$-cycloalkyl, —NHCO$_2$-aryl, —NHCO$_2$-heteroaryl, —NHCO$_2$-heterocycloalkyl, —NHC(O)NH$_2$, NHC(O)NH—$C_1$–$C_{12}$-alkyl, —NHC(O)NH—$C_2$–$C_{12}$-alkenyl, —NHC(O)NH—$C_2$–$C_{12}$-alkenyl, —NHC(O)NH—$C_3$–$C_{12}$-cycloalkyl, —NHC(O)NH-aryl, —NHC(O)NH-heteroaryl, —NHC(O)NH-heterocycloalkyl, NHC(S)NH$_2$, NHC(S)NH—$C_1$–$C_{12}$-alkyl, —NHC(S)NH—$C_2$–$C_{12}$-alkenyl, —NHC(S)NH—$C_2$–$C_{12}$-alkenyl, —NHC(S)NH—$C_3$–$C_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—$C_1$–$C_{12}$-alkyl, —NHC(NH)NH—$C_2$–$C_{12}$-alkenyl, —NHC(NH)NH—$C_2$–$C_{12}$-alkenyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_{12}$-alkyl, —NHC(NH)—$C_2$–$C_{12}$-alkenyl, —NHC(NH)—$C_2$–$C_{12}$-alkenyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkenyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, —S(O)—$C_3$–$C_{12}$-cycloalkyl, —S(O)-aryl, —S(O)-heteroaryl, —S(O)-heterocycloalkyl-SO$_2$NH$_2$, —SO$_2$NH—$C_1$–$C_{12}$-alkyl, —SO$_2$NH—$C_2$–$C_{12}$-alkenyl, —SO$_2$NH—$C_2$–$C_{12}$-alkenyl, —SO$_2$NH—$C_3$–$C_{12}$-cycloalkyl, —SO$_2$NH-aryl, —SO$_2$NH-heteroaryl, —SO$_2$NH-heterocycloalkyl, —NHSO$_2$—$C_1$–$C_{12}$-alkyl, —NHSO$_2$—$C_2$–$C_{12}$-alkenyl, —NHSO$_2$—$C_2$–$C_{12}$-alkenyl, —NHSO$_2$—$C_3$–$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$–$C_{12}$-cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The terms "$C_2$–$C_{12}$ alkenyl" or "$C_2$–$C_6$ alkenyl," as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, and the like.

The term "substituted alkenyl," as used herein, refers to a "$C_2$–$C_{12}$ alkenyl" or "$C_2$–$C_6$ alkenyl" group as previously defined, substituted by independent replacement or one, two, or three of the hydrogen atoms thereon with substituents including, but not limited to, —F, —Cl, —Br, —I, —OH, protected hydroxy, —NO$_2$, —CN, —$C_1$–$C_{12}$-alkyl optionally substituted with halogen, $C_2$–$C_{12}$-alkenyl optionally substituted with halogen, —$C_2$–$C_{12}$-alkynyl optionally substituted with halogen, —NH$_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, diheteroarylamino, —O—$C_1$–$C_{12}$-alkyl, —O—$C_2$–$C_{12}$-alkenyl, —O—$C_2$–$C_{12}$-alkenyl, —O—$C_3$–$C_{12}$-cycloalkyl, —O-aryl, —O-heteroaryl, —O-heterocycloalkyl, —C(O)—$C_1$–$C_{12}$-alkyl, —C(O)—$C_2$–$C_{12}$-alkenyl, —C(O)—$C_2$–$C_{12}$-alkenyl, —C(O)—$C_3$–$C_{12}$-cycloalkyl, —C(O)-aryl, —C(O)-heteroaryl, —C(O)-heterocycloalkyl, —CONH$_2$, —CONH—$C_1$–$C_{12}$-alkyl, —CONH—$C_2$–$C_{12}$-alkenyl, —CONH—$C_2$–$C_{12}$-alkenyl, —CONH—$C_3$–$C_{12}$-cycloalkyl, —CONH-aryl, —CONH-heteroaryl, —CONH-heterocycloalkyl, —OCO$_2$—$C_1$–$C_{12}$-alkyl, —OCO$_2$—$C_2$–$C_{12}$-alkenyl, —OCO$_2$—$C_2$–$C_{12}$-alkenyl, —OCO$_2$—$C_3$–$C_{12}$-cycloalkyl, —OCO$_2$-aryl, —OCO$_2$-heteroaryl, —OCO$_2$-heterocycloalkyl, —OCONH$_2$, —OCONH—$C_1$–$C_{12}$-alkyl, —OCONH—$C_2$–$C_{12}$-alkenyl, —OCONH—$C_2$–$C_{12}$-alkenyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkenyl, —NHC(O)—$C_3$–$C_{12}$-cycloalkyl, —NHC(O)-aryl, —NHC(O)-heteroaryl, —NHC(O)-heterocycloalkyl, —NHCO$_2$—$C_1$–$C_{12}$-alkyl, —NHCO$_2$—$C_2$–$C_{12}$-alkenyl, —NHCO$_2$—$C_2$–$C_{12}$-alkenyl, —NHCO$_2$—$C_3$–$C_{12}$-cycloalkyl, —NHCO$_2$-aryl, —NHCO$_2$-heteroaryl, —NHCO$_2$-heterocycloalkyl, —NHC(O)NH$_2$, NHC(O)NH—$C_1$–$C_{12}$-alkyl, —NHC(O)NH—$C_2$–$C_{12}$-alkenyl, —NHC(O)NH—$C_2$–$C_{12}$-alkenyl, —NHC(O)NH—$C_3$–$C_{12}$-cycloalkyl, —NHC(O)NH-aryl, —NHC(O)NH-heteroaryl, —NHC(O)NH-heterocycloalkyl, NHC(S)NH$_2$, NHC(S)NH—$C_1$–$C_{12}$-alkyl, —NHC(S)NH—$C_2$–$C_{12}$-alkenyl, —NHC(S)NH—$C_2$–$C_{12}$-alkenyl, —NHC(S)NH—$C_3$–$C_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—$C_1$–$C_{12}$-alkyl, —NHC(NH)NH—$C_2$–$C_{12}$-alkenyl, —NHC(NH)NH—$C_2$–$C_{12}$-alkenyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_{12}$-alkyl, —NHC(NH)—$C_2$–$C_{12}$-alkenyl, —NHC(NH)—$C_2$–$C_{12}$-alkenyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkenyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, —S(O)—$C_3$–$C_{12}$-cycloalkyl, —S(O)-aryl, —S(O)-heteroaryl, —S(O)-heterocycloalkyl —SO$_2$NH$_2$, —SO$_2$NH—$C_1$–$C_{12}$-alkyl, —SO$_2$NH—$C_2$–$C_{12}$-alkenyl, —SO$_2$NH—$C_2$–$C_{12}$-alkenyl, —SO$_2$NH—$C_3$–$C_{12}$-cycloalkyl, —SO$_2$NH-aryl, —SO$_2$NH-heteroaryl, —SO$_2$NH-heterocycloalkyl, —NHSO$_2$—$C_1$–$C_{12}$-alkyl, —NHSO$_2$—$C_2$–$C_{12}$-alkenyl, —NHSO$_2$—$C_2$–$C_{12}$-alkenyl, —NHSO$_2$—$C_3$–$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$–$C_{12}$-cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The terms "$C_2$–$C_{12}$ alkynyl" or "$C_2$–$C_6$ alkynyl," as used herein, denote a monovalent group derived from a hydrocarbon moiety containing from two to twelve or two to six carbon atoms having at least one carbon-carbon triple bond by the removal of a single hydrogen atom. Representative alkynyl groups include, but are not limited to, for example, ethynyl, 1-propynyl, 1-butynyl, and the like.

The term "substituted alkynyl," as used herein, refers to a "$C_2$–$C_{12}$ alkynyl" or "$C_2$–$C_6$ alkynyl" group as previously defined, substituted by independent replacement or one, two, or three of the hydrogen atoms thereon with substituents including, but not limited to, —F, —Cl, —Br, —I, —OH, protected hydroxy, —NO$_2$, —CN, —C$_1$–C$_{12}$-alkyl optionally substituted with halogen, C$_2$–C$_{12}$-alkenyl optionally substituted with halogen, —C$_2$–C$_{12}$-alkynyl optionally substituted with halogen, —NH$_2$, protected amino, —NH—C$_1$–C$_{12}$-alkyl, —NH—C$_2$–C$_{12}$-alkenyl, —NH—C$_2$–C$_{12}$-alkenyl, —NH—C$_3$–C$_{12}$-cycloalkyl, —NH-aryl, —NH-heteroaryl, —NH-heterocycloalkyl, -dialkylamino, -diarylamino, -diheteroarylamino, —O—C$_1$–C$_{12}$-alkyl, —O—C$_2$–C$_{12}$-alkenyl, —O—C$_2$–C$_{12}$-alkenyl, —O—C$_3$–C$_{12}$-cycloalkyl, —O-aryl, —O-heteroaryl, —O-heterocycloalkyl, —C(O)—C$_1$–C$_{12}$-alkyl, —C(O)—C$_2$–C$_{12}$-alkenyl, —C(O)—C$_2$–C$_{12}$-alkenyl, —C(O)—C$_3$–C$_{12}$-cycloalkyl, —C(O)-aryl, —C(O)-heteroaryl, —C(O)-heterocycloalkyl, —CONH$_2$, —CONH—C$_1$–C$_{12}$-alkyl, —CONH—C$_2$–C$_{12}$-alkenyl, —CONH—C$_2$–C$_{12}$-alkenyl, —CONH—C$_3$–C$_{12}$-cycloalkyl, —CONH-aryl, —CONH-heteroaryl, —CONH-heterocycloalkyl, —OCO$_2$—C$_1$–C$_{12}$-alkyl, —OCO$_2$—C$_2$–C$_{12}$-alkenyl, —OCO$_2$—C$_2$–C$_{12}$-alkenyl, —OCO$_2$—C$_3$–C$_{12}$-cycloalkyl, —OCO$_2$-aryl, —OCO$_2$-heteroaryl, —OCO$_2$-heterocycloalkyl, —OCONH$_2$, —OCONH—C$_1$–C$_{12}$-alkyl, —OCONH—C$_2$–C$_{12}$-alkenyl, —OCONH—C$_2$–C$_{12}$-alkenyl, —OCONH—C$_3$–C$_{12}$-cycloalkyl, —OCONH-aryl, —OCONH-heteroaryl, —OCONH-heterocycloalkyl, —NHC(O)—C$_1$–C$_{12}$-alkyl, —NHC(O)—C$_2$–C$_{12}$-alkenyl, —NHC(O)—C$_2$–C$_{12}$-alkenyl, —NHC(O)—C$_3$–C$_{12}$-cycloalkyl, —NHC(O)-aryl, —NHC(O)-heteroaryl, —NHC(O)-heterocycloalkyl, —NHCO$_2$—C$_1$–C$_{12}$-alkyl, —NHCO$_2$—C$_2$–C$_{12}$-alkenyl, —NHCO$_2$—C$_2$–C$_{12}$-alkenyl, —NHCO$_2$—C$_3$–C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$–C$_{12}$-alkyl, —NHC(O)NH—C$_2$–C$_{12}$-alkenyl, —NHC(O)NH—C$_2$–C$_{12}$-alkenyl, —NHC(O)NH—C$_3$–C$_{12}$-cycloalkyl, —NHC(O)NH-aryl, —NHC(O)NH-heteroaryl, —NHC(O)NH-heterocycloalkyl, NHC(S)NH$_2$, NHC(S)NH—C$_1$–C$_{12}$-alkyl, —NHC(S)NH—C$_2$–C$_{12}$-alkenyl, —NHC(S)NH—C$_2$–C$_{12}$-alkenyl, —NHC(S)NH—C$_3$–C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$–C$_{12}$-alkenyl, —NHC(NH)NH—C$_2$–C$_{12}$-alkenyl, —NHC(NH)NH—C$_2$–C$_{12}$-alkenyl, —NHC(NH)NH—C$_3$–C$_{12}$-cycloalkyl, —NHC(NH)NH-aryl, —NHC(NH)NH-heteroaryl, —NHC(NH)NH-heterocycloalkyl, NHC(NH)—C$_{1-C12}$-alkyl, —NHC(NH)—C$_2$–C$_{12}$-alkenyl, —NHC(NH)—C$_2$–C$_{12}$-alkenyl, —NHC(NH)—C$_3$–C$_{12}$-cycloalkyl, —NHC(NH)-aryl, —NHC(NH)-heteroaryl, —NHC(NH)-heterocycloalkyl, —C(NH)NH—C$_1$–C$_{12}$-alkyl, —C(NH)NH—C$_2$–C$_{12}$-alkenyl, —C(NH)NH—C$_2$–C$_{12}$-alkenyl, —C(NH)NH—C$_3$–C$_{12}$-cycloalkyl, —C(NH)NH-aryl, —C(NH)NH-heteroaryl, —C(NH)NH-heterocycloalkyl, —S(O)—C$_1$–C$_{12}$-alkyl, —S(O)—C$_2$–C$_{12}$-alkenyl, —S(O)—C$_2$–C$_{12}$-alkenyl, —S(O)—C$_3$–C$_{12}$-cycloalkyl, —S(O)-aryl, —S(O)-heteroaryl, —S(O)-heterocycloalkyl —SO$_2$NH$_2$, —SO$_2$NH—C$_1$–C$_{12}$-alkyl, —SO$_2$NH—C$_2$–C$_{12}$-alkenyl, —SO$_2$NH—C$_2$–C$_{12}$-alkenyl, —SO$_2$NH—C$_3$–C$_{12}$-cycloalkyl, —SO$_2$NH-aryl, —SO$_2$NH-heteroaryl, —SO$_2$NH-heterocycloalkyl, —NHSO$_2$—C$_1$–C$_{12}$-alkyl, —NHSO$_2$—C$_2$–C$_{12}$-alkenyl, —NHSO$_2$—C$_2$–C$_{12}$-alkenyl, —NHSO$_2$—C$_3$–C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$–C$_{12}$-cycloalkyl, -methoxymethoxy, -methoxyethoxy, —SH, —S—C$_1$–C$_{12}$-alkyl, —S—C$_2$–C$_{12}$-alkenyl, —S—C$_2$–C$_{12}$-alkenyl, —S—C$_3$–C$_{12}$-cycloalkyl, —S-aryl, —S-heteroaryl, —S-heterocycloalkyl, or methylthiomethyl.

The term "C$_1$–C$_6$ alkoxy," as used herein, refers to a C$_1$–C$_6$ alkyl group, as previously defined, attached to the parent molecular moiety through an oxygen atom. Examples of C$_1$–C$_6$-alkoxy include, but are not limited to, methoxy, ethoxy, propoxy, isopropoxy, n-butoxy, tert-butoxy, neopentoxy and n-hexoxy.

The terms "halo" and "halogen," as used herein, refer to an atom selected from fluorine, chlorine, bromine and iodine.

The term "aryl," as used herein, refers to a mono- or bicyclic carbocyclic ring system having one or two aromatic rings including, but not limited to, phenyl, naphthyl, tetrahydronaphthyl, indanyl, idenyl and the like.

The term "substituted aryl," as used herein, refers to an aryl group, as previously defined, substituted by independent replacement or one, two, or three of the hydrogen atoms thereon with substituents including, but not limited to, —F, —Cl, —Br, —I, —OH, protected hydroxy, —NO$_2$, —CN, —C$_1$–C$_{12}$-alkyl optionally substituted with halogen, C$_2$–C$_{12}$-alkenyl optionally substituted with halogen, —C$_2$–C$_{12}$-alkynyl optionally substituted with halogen, —NH$_2$, protected amino, —NH—C$_1$–C$_{12}$-alkyl, —NH—C$_2$–C$_{12}$-alkenyl, —NH—C$_2$–C$_{12}$-alkenyl, —NH, —C$_3$–C$_{12}$-cycloalkyl, —NH-aryl, —NH-heteroaryl, —NH-heterocycloalkyl, -dialkylamino, -diarylamino, diheteroarylamino, —O—C$_1$–C$_{12}$-alkyl, —O—C$_2$–C$_{12}$-alkenyl, —O—C$_2$–C$_{12}$-alkenyl, —O—C$_3$–C$_{12}$-cycloalkyl, —O-aryl, —O-heteroaryl, —O-heterocycloalkyl, —C(O)—C$_1$–C$_{12}$-alkyl, —C(O)—C$_2$–C$_{12}$-alkenyl, —C(O)—C$_2$–C$_{12}$-alkenyl, —C(O)—C$_3$–C$_{12}$-cycloalkyl, —C(O)-aryl, —C(O)-heteroaryl, —C(O)-heterocycloalkyl, —CONH$_2$, —CONH—C$_1$–C$_{12}$-alkyl, —CONH—C$_2$–C$_{12}$-alkenyl, —CONH—C$_2$–C$_{12}$-alkenyl, —CONH-C$_3$–C$_{12}$-cycloalkyl, —CONH-aryl, —CONH-heteroaryl, —CONH-heterocycloalkyl, —OCO$_2$—C$_1$–C$_{12}$-alkyl, —OCO$_2$—C$_2$–C$_{12}$-alkenyl, —OCO$_2$—C$_2$–C$_{12}$-alkenyl, —OCO$_2$—C$_3$–C$_{12}$-cycloalkyl, —OCO$_2$-aryl, —OCO$_2$-heteroaryl, —OCO$_2$-heterocycloalkyl, —OCONH$_2$, —OCONH—C$_1$–C$_{12}$-alkyl, —OCONH—C$_2$–C$_{12}$-alkenyl, —OCONH—C$_3$–C$_{12}$-cycloalkyl, —OCONH-aryl, —OCONH-heteroaryl, —OCONH-heterocycloalkyl, —NHC(O)—C$_1$–C$_{12}$-alkyl, —NHC(O)—C$_2$–C$_{12}$-alkenyl, —NHC(O)—C$_2$–C$_{12}$-alkenyl, —NHC(O)—C$_3$–C$_{12}$-cycloalkyl, —NHC(O)-aryl, —NHC(O)-heteroaryl, —NHC(O)-heterocycloalkyl, —NHCO$_2$—C$_1$–C$_{12}$-alkyl, —NHCO$_2$—C$_2$–C$_{12}$-alkenyl, —NHCO$_2$—C$_3$–C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$–C$_{12}$-alkyl, —NHC(O)NH—C$_2$–C$_{12}$-alkenyl, —NHC(O)NH—C$_2$–C$_{12}$-alkenyl, —NHC(O)NH—C$_3$–C$_{12}$-cycloalkyl, —NHC(O)NH-aryl, —NHC(O)NH-heteroaryl, —NHC(O)NH-heterocycloalkyl, NHC(S)NH$_2$, NHC(S)NH—C$_1$–C$_{12}$-alkyl, —NHC(S)NH—C$_2$–C$_{12}$-alkenyl, —NHC(S)NH—C$_2$–C$_{12}$-alkenyl, —NHC(S)NH—C$_3$–C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$–C$_{12}$-alkyl, —NHC(NH)NH—C$_2$–C$_{12}$-alkenyl, —NHC(NH)NH—C$_2$–C$_{12}$-alkenyl, —NHC(NH)NH—C$_3$–C$_{12}$-cycloalkyl, —NHC(NH)NH-aryl, —NHC(NH)NH-heteroaryl, —NHC(NH)NH-heterocycloalkyl, NHC(NH)—C$_1$–C$_{12}$-alkyl, —NHC(NH)—C$_2$–C$_{12}$-alkenyl, —NHC(NH)—C$_2$–C$_{12}$-alkenyl, —NHC(NH)—C$_3$–C$_{12}$-cycloalkyl, —NHC(NH)-aryl, —NHC(NH)-heteroaryl, —NHC(NH)-heterocycloalkyl, —C(NH)NH—C$_1$–C$_{12}$-alkyl, —C(NH)NH—C$_2$–C$_{12}$-alkenyl, C(NH)NH—C$_2$–C$_{12}$-alkenyl, —C(NH)NH—C$_3$–C$_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, —S(O)—$C_3$–$C_{12}$-cycloalkyl, —S(O)-aryl, —S(O)-heteroaryl, —S(O)-heterocycloalkyl —$SO_2NH_2$, —$SO_2$NH—$C_1$–$C_{12}$-alkyl, —$SO_2$NH—$C_2$–$C_{12}$-alkenyl, —$SO_2$NH—$C_2$–$C_{12}$-alkenyl, —$SO_2$NH—$C_3$–$C_{12}$-cycloalkyl, —$SO_2$NH-aryl, —$SO_2$NH-heteroaryl, —$SO_2$NH-heterocycloalkyl, —$NHSO_2$—$C_1$–$C_{12}$-alkyl, —$NHSO_2$—$C_2$–$C_{12}$-alkenyl, —$NHSO_2$—$C_2C_{12}$-alkenyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$–$C_{12}$-cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The term "arylalkyl," as used herein, refers to a $C_1$–$C_3$ alkyl or $C_1$–$C_6$ alkyl residue attached to an aryl ring. Examples include, but are not limited to, benzyl, phenethyl and the like.

The term "substituted arylalkyl," as used herein, refers to an arylalkyl group, as previously defined, substituted by independent replacement or one, two, or three of the hydrogen atoms thereon with substituents including, but not limited to, but not limited to, —F, —Cl, —Br, —I, —OH, protected hydroxy, —$NO_2$, —CN, —$C_1$–$C_{12}$-alkyl optionally substituted with halogen, $C_2$–$C_{12}$-alkenyl optionally substituted with halogen, —$C_2$–$C_{12}$-alkynl optionally substituted with halogen, —$NH_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, —O—$C_2$–$C_{12}$-alkenyl, —O—$C_3C_{12}$-cycloalkyl, —O-aryl, —O-heteroaryl, —O-heterocycloalkyl, —C(O)—$C_1$–$C_{12}$-alkyl, —C(O)—$C_2$–$C_{12}$-alkenyl, —C(O)—$C_2$–$C_{12}$-alkenyl, —C(O)—$C_3$–$C_{12}$-cycloalkyl, —C(O)-aryl, —C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkenyl, —CONH—$C_3$–$C_{12}$-cycloalkyl, —CONH-aryl, —CONH-heteroaryl, —CONH-heterocycloalkyl, —$OCO_2$—$C_1$–$C_{12}$-alkyl, —$OCO_2$—$C_2$–$C_{12}$-alkenyl, —$OCO_2$—$C_2$–$C_{12}$-alkenyl —$OCO_2$—$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkenyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkenyl, —NHC(O)—$C_3$–$C_{12}$-cycloalkyl, —NHC(O)-aryl, —NHC(O)-heteroaryl, —NHC(O)-heterocycloalkyl, —$NHCO_2$—$C_1$–$C_{12}$-alkyl, —$NHCO_2$—$C_2$–$C_{12}$-alkenyl, —$NHCO_2$—$C_2$–$C_{12}$-alkenyl, —$NHCO_2$—$C_3$–$C_{12}$-cycloalkyl, —$NHCO_2$-aryl, —$NHCO_2$-heteroaryl, —$NHCO_2$-heterocycloalkyl, —NHC(O)$NH_2$, NHC(O)NH—$C_1$–$C_{12}$-alkyl, —NHC(O)NH—$C_2$–$C_{12}$-alkenyl, —NHC(O)NH—$C_2$–$C_{12}$-alkenyl, —NHC(O)NH—$C_3$–$C_{12}$-cycloalkyl, —NHC(O)NH-aryl, —NHC(O)NH-heteroaryl, —NHC(O)NH-heterocycloalkyl, NHC(S)$NH_2$, NHC(S)NH—$C_1$–$C_{12}$-alkyl, —NHC(S)NH—$C_2$–$C_{12}$-alkenyl, —NHC(S)NH—$C_2$–$C_{12}$-alkenyl, —NHC(S)NH—$C_3$–$C_{12}$-cycloalkyl, —NHC(S)NH-aryl, —NHC(S)NH-heteroaryl, —NHC(S)NH-heterocycloalkyl, —NHC(NH)$NH_2$, NHC(NH)NH—$C_1$–$C_{12}$-alkyl, —NHC(NH)NH—$C_2$–$C_{12}$-alkenyl, —NHC(NH)NH—$C_2$–$C_{12}$-alkenyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_{12}$-alkyl, —NHC(NH)—$C_2$–$C_{12}$-alkenyl, —NHC(NH)—$C_2$–$C_{12}$-alkenyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkenyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, S(O)—$C_3$–$C_{12}$-cycloalkyl, —S(O)-aryl, —S(O)-heteroaryl, —S(O)-heterocycloalkyl —$SO_2NH_2$, —$SO_2$NH—$C_1$–$C_{12}$-alkyl, —$SO_2$NH—$C_2$–$C_{12}$-alkenyl, —$SO_2$NH—$C_2$–$C_{12}$-alkenyl, —$SO_2$NH—$C_3$–$C_{12}$-cycloalkyl, —$SO_2$NH-aryl, —$SO_2$NH-heteroaryl, —$SO_2$NH-heterocycloalkyl, —$NHSO_2$—$C_1$–$C_{12}$-alkyl, —$NHSO_2$—$C_2$–$C_{12}$-alkenyl, —$NHSO_2C_2$–$C_{12}$-alkenyl, —$NHSO_2$—$C_3$–$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$–$C_{12}$-cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The term "heteroaryl," as used herein, refers to a mono-, bi-, or tri-cyclic aromatic radical or ring having from five to ten ring atoms of which one ring atom is selected from S, O and N; zero, one or two ring atoms are additional heteroatoms independently selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "substituted heteroaryl," as used herein, refers to a heteroaryl group as previously defined, substituted by independent replacement or one, two, or three of the hydrogen atoms thereon with substituents including, but not limited to, —F, —Cl, —Br, —I, —OH, protected hydroxy, —$NO_2$, —CN, —$C_1$–$C_{12}$-alkyl optionally substituted with halogen, $C_2$–$C_{12}$-alkenyl optionally substituted with halogen, —$C_2$–$C_{12}$-alkynyl optionally substituted with halogen, —$NH_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, O—$C_2$–$C_{12}$-alkenyl, —O—$C_3$–$C_{12}$-cycloalkyl, —O-aryl, —O-heteroaryl, —O-heterocycloalkyl, —C(O)—$C_1$–$C_{12}$-alkyl, —C(O)—$C_2$–$C_{12}$-alkenyl, —C(O)—$C_2$–$C_{12}$-alkenyl, —C(O)—$C_3$–$C_{12}$-cycloalkyl, —C(O)-aryl, —C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkenyl, —CONH—$C_3$–$C_{12}$-cycloalkyl, —CONH-aryl, —CONH-heteroaryl, —CONH-heterocycloalkyl, —$OCO_2$—$C_1$–$C_{12}$-alkyl, —$OCO_2$—$C_2$–$C_{12}$-alkenyl, —$OCO_2$—$C_2$–$C_{12}$-alkenyl, —$OCO_2$—$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkenyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—

$C_2$–$C_{12}$-alkenyl, —NHC(O)—$C_2$–$C_{12}$-alkenyl, —NHC(O)—$C_3$–$C_{12}$-cycloalkyl, —NHC(O)-aryl, —NHC(O)-heteroaryl, —NHC(O)-heterocycloalkyl, —NHCO$_2$—$C_1$–$C_{12}$-alkyl, —NHCO$_2$—$C_2$–$C_{12}$-alkenyl, —NHCO$_2$—$C_2$–$C_{12}$-alkenyl, —NHCO$_2$—$C_3$–$C_{12}$-cycloalkyl, —NHCO-aryl, —NHCO$_2$-heteroaryl, —NHCO$_2$-heterocycloalkyl, —NHC(O)NH$_2$, NHC(O)NH—$C_1$–$C_{12}$-alkyl, —NHC(O)NH—$C_2$–$C_{12}$-alkenyl, —NHC(O)NH—$C_2$–$C_{12}$-alkenyl, —NHC(O)NH—$C_3$–$C_{12}$-cycloalkyl, —NHC(O)NH-aryl, —NHC(O)NH-heteroaryl, —NHC(O)NH-heterocycloalkyl, NHC(S)NH$_2$, NHC(S)NH—$C_1$–$C_{12}$-alkyl, —NHC(S)NH—$C_2$–$C_{12}$-alkenyl, —NHC(S)NH—$C_2$–$C_{12}$-alkenyl, —NHC(S)NH—$C_3$–$C_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—$C_1$–$C_{12}$-alkyl, —NHC(NH)NH—$C_2$–$C_{12}$-alkenyl, —NHC(NH)NH—$C_2$–$C_{12}$-alkenyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_{12}$-alkyl, —NHC(NH)—$C_2$–$C_{12}$-alkenyl, —NHC(NH)—$C_2$–$C_{12}$-alkenyl, —NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkenyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, —S(O)—$C_3$–$C_{12}$-cycloalkyl, —S(O)-aryl, —S(O)-heteroaryl, —S(O)-heterocycloalkyl —SO$_2$NH$_2$, —SO$_2$NH—$C_1$–$C_{12}$-alkyl, —SO$_2$NH—$C_2$–$C_{12}$-alkenyl, —SO$_2$NH—$C_2$–$C_{12}$-alkenyl, —SO$_2$NH—$C_3$–$C_{12}$-cycloalkyl, —SO$_2$NH-aryl, —SO$_2$NH-heteroaryl, —SO$_2$NH-heterocycloalkyl, —NHSO$_2$—$C_1$–$C_{12}$-alkyl, —NHSO$_2$—$C_2$–$C_{12}$-alkenyl; —NHSO$_2$$C_2$–$C_{12}$-alkenyl, —NHSO$_2$—$C_3$–$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$–$C_{12}$-cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$$C_{12}$-cycloalkyl, —S-aryl, —S-heteroaryl, —S-heterocycloalkyl, or methylthiomethyl.

The term "$C_3$–$C_{12}$-cycloalkyl," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl.

The term "substituted $C_3$–$C_{12}$-cycloalkyl," as used herein, refers to a $C_3$–$C_{12}$-cycloalkyl group as previously defined, substituted by independent replacement or one, two, or three of the hydrogen atoms thereon with substituents including, but not limited to, —F, —Cl, —Br, —I, —OH, protected hydroxy, —NO$_2$, —CN, —$C_1$–$C_{12}$-alkyl optionally substituted with halogen, $C_2$–$C_{12}$-alkenyl optionally substituted with halogen, —$C_2$–$C_{12}$-alkynyl optionally substituted with halogen, —NH$_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, —O—$C_2$–$C_{12}$-alkenyl, —O—$C_3$–$C_{12}$-cycloalkyl, —O-aryl, —O-heteroaryl, —O-heterocycloalkyl, —C(O)—$C_1$–$C_{12}$-alkyl, C(O)—$C_2$–$C_{12}$-alkenyl, —C(O)—$C_2$–$C_{12}$-alkenyl, —C(O)—$C_3$–$C_{12}$-cycloalkyl, —C(O)-aryl, —C(O)-heteroaryl, —C(O)-heterocycloalkyl, —CONH$_2$, —CONH—$C_1$–$C_{12}$-alkyl, —CONH—$C_2$–$C_{12}$-alkenyl, —CONH—$C_2$–$C_{12}$-alkenyl, —CONH—$C_3$–$C_{12}$-cycloalkyl, —CONH-aryl, —CONH-heteroaryl, —CONH-heterocycloalkyl, —OCO$_2$—$C_1$–$C_{12}$-alkyl, —OCO$_2$—$C_2$–$C_{12}$-alkenyl, —OCO$_2$—$C_2$–$C_{12}$-alkenyl, —OCO$_2$—$C_3$–$C_{12}$-cycloalkyl, —OCO$_2$-aryl, —OCO$_2$-heteroaryl, —OCO$_2$-heterocycloalkyl, —OCONH$_2$, —OCONH—$C_1$–$C_{12}$-alkyl, —OCONH—$C_2$–$C_{12}$-alkenyl, —OCONH—$C_2$–$C_{12}$-alkenyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkenyl, —NHC(O)—$C_3$–$C_{12}$-cycloalkyl, —NHC(O)-aryl, —NHC(O)-heteroaryl, —NHC(O)-heterocycloalkyl, —NHCO$_2$—$C_1$–$C_{12}$-alkyl, —NHCO$_2$—$C_2$–$C_{12}$-alkenyl, —NHCO$_2$—$C_2$–$C_{12}$-alkenyl, —NHCO$_2$—$C_3$–$C_{12}$-cycloalkyl, —NHCO$_2$-aryl, —NHCO$_2$-heteroaryl, —NHCO$_2$-heterocycloalkyl, —NHC(O)NH$_2$, NHC(O)NH—$C_1$–$C_{12}$-alkyl, —NHC(O)NH—$C_2$–$C_{12}$-alkenyl, —NHC(O)NH—$C_2$–$C_{12}$-alkenyl, —NHC(O)NH—$C_3$–$C_{12}$-cycloalkyl, —NHC(O)NH-aryl, —NHC(O)NH-heteroaryl, —NHC(O)NH-heterocycloalkyl, NHC(S)NH$_2$, NHC(S)NH—$C_1$–$C_{12}$-alkyl, —NHC(S)NH—$C_2$–$C_{12}$-alkenyl, —NHC(S)NH—$C_2$–$C_{12}$-alkenyl, —NHC(S)NH—$C_3$–$C_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—$C_1$–$C_{12}$-alkyl, —NHC(NH)NH—$C_2$–$C_{12}$-alkenyl, —NHC(NH)NH—$C_2$–$C_{12}$-alkenyl, —NHC(NH)NH—$C_3$–$C_{12}$-cycloalkyl, —NHC(NH)NH-aryl, —NHC(NH)NH-heteroaryl, —NHC(NH)NH-heterocycloalkyl, NHC(NH)—$C_1$–$C_{12}$-alkyl, —NHC(NH)—$C_2$–$C_{12}$-alkenyl, —NHC(NH)—$C_2$–$C_{12}$-alkenyl, NHC(NH)—$C_3$–$C_{12}$-cycloalkyl, —NHC(NH)-aryl, —NHC(NH)-heteroaryl, —NHC(NH)-heterocycloalkyl, —C(NH)NH—$C_1$–$C_{12}$-alkyl, —C(NH)NH—$C_2$–$C_{12}$-alkenyl, —C(NH)NH—$C_2$–$C_{12}$-alkenyl, —C(NH)NH—$C_3$–$C_{12}$-cycloalkyl, —C(NH)NH-aryl, —C(NH)NH-heteroaryl, —C(NH)NH-heterocycloalkyl, —S(O)—$C_1$–$C_{12}$-alkyl, —S(O)—$C_2$–$C_{12}$-alkenyl, —S(O)—$C_2$–$C_{12}$-alkenyl, —S(O)—$C_3$–$C_{12}$-cycloalkyl, —S(O)-aryl, —S(O)-heteroaryl, —S(O)-heterocycloalkyl —SO$_2$NH$_2$, —SO$_2$NH—$C_1$–$C_{12}$-alkyl, —SO$_2$NH—$C_2$–$C_{12}$-alkenyl, —SO$_2$NH—$C_2$–$C_{12}$-alkenyl, —SO$_2$NH—$C_3$–$C_{12}$-cycloalkyl, —SO$_2$NH-aryl, —SO$_2$NH-heteroaryl, —SO$_2$NH-heterocycloalkyl, —NHSO$_2$—$C_1$–$C_{12}$-alkyl, —NHSO$_2$—$C_2$–$C_{12}$-alkenyl, —NHSO$_2$—$C_2$–$C_{12}$-alkenyl, —NHSO$_2$—$C_3$–$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$–$C_{12}$-cycloalkyl, -methoxymethoxy, -methoxyethoxy, —SH, —S—$C_1$–$C_{12}$-alkyl, —S—$C_2$–$C_{12}$-alkenyl, —S—$C_2$–$C_{12}$-alkenyl, —S—$C_3$–$C_{12}$-cycloalkyl, —S-aryl, —S-heteroaryl, —S-heterocycloalkyl, or methylthiomethyl.

The term "heterocycloalkyl," as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "substituted heterocycloalkyl," as used herein, refers to a heterocycloalkyl group, as previously defined, substituted by independent replacement or one, two, or three of the hydrogen atoms thereon with substituents including, but not limited to, —F, —Cl, —Br, —I, —OH, protected hydroxy, —NO$_2$, —CN, —C$_1$–C$_{12}$-alkyl optionally substituted with halogen, C$_2$–C$_{12}$-alkenyl optionally substituted with halogen, —C$_2$–C$_{12}$-alkynyl optionally substituted with halogen, —NH$_2$, protected amino, —NH—C$_1$–C$_{12}$-alkyl, —NH—C$_2$–C$_{12}$-alkenyl, —NH—C$_2$–C$_{12}$-alkenyl, —NH—C$_3$–C$_{12}$-cycloalkyl, —NH-aryl, —NH-heteroaryl, —NH-heterocycloalkyl, -dialkylamino, -diarylamino, -diheteroarylamino, —O—C$_1$–C$_{12}$-alkyl, —O—C$_2$–C$_{12}$-alkenyl, —O—C$_2$–C$_{12}$-alkenyl, —O—C$_3$–C$_{12}$-cycloalkyl, —O-aryl, —O-heteroaryl, —O-heterocycloalkyl, —C(O)—C$_1$–C$_{12}$-alkyl, —C(O)—C$_2$–C$_{12}$-alkenyl, —C(O)—C$_2$–C$_{12}$-alkenyl, —C(O)—C$_3$–C$_{12}$-cycloalkyl, —C(O)-aryl, —C(O)-heteroaryl, —C(O)-heterocycloalkyl, —CONH$_2$, —CONH—C$_1$–C$_{12}$-alkyl, —CONH—C$_2$–C$_{12}$-alkenyl, —CONH—C$_2$–C$_{12}$-alkenyl, —CONH—C$_3$–C$_{12}$-cycloalkyl, —CONH-aryl, —CONH-heteroaryl, —CONH-heterocycloalkyl, —OCO$_2$—C$_1$–C$_{12}$-alkyl, —OCO$_2$—C$_2$–C$_{12}$-alkenyl, —OCO$_2$—C$_2$–C$_{12}$-alkenyl, —OCO$_2$—C$_3$–C$_{12}$-cycloalkyl, —OCO$_2$-aryl, —OCO$_2$-heteroaryl, —OCO$_2$-heterocycloalkyl, —OCONH$_2$, —OCONH—C$_1$–C$_{12}$-alkyl, —OCONH—C$_2$–C$_{12}$-alkenyl, —OCONH—C$_2$–C$_{12}$-alkenyl, —OCONH—C$_3$–C$_{12}$-cycloalkyl, —OCONH-aryl, —OCONH-heteroaryl, —OCONH-heterocycloalkyl, —NHC(O)—C$_1$–C$_{12}$-alkyl, —NHC(O)—C$_2$–C$_{12}$-alkenyl, —NHC(O)—C$_2$–C$_{12}$-alkenyl, —NHC(O)—C$_3$–C$_{12}$-cycloalkyl, —NHC(O)-aryl, —NHC(O)-heteroaryl, —NHC(O)-heterocycloalkyl, —NHCO$_2$—C$_1$–C$_{12}$-alkyl, —NHCO$_2$—C$_2$–C$_{12}$-alkenyl, —NHCO$_2$—C$_2$–C$_{12}$-alkenyl, —NHCO$_2$—C$_3$–C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$–C$_{12}$-alkyl, —NHC(O)NH—C$_2$–C$_{12}$-alkenyl, —NHC(O)NH—C$_2$–C$_{12}$-alkenyl, —NHC(O)NH—C$_3$–C$_{12}$-cycloalkyl, —NHC(O)NH-aryl, —NHC(O)NH-heteroaryl, —NHC(O)NH-heterocycloalkyl, NHC(S)NH$_2$, NHC(S)NH—C$_1$–C$_{12}$-alkyl, —NHC(S)NH—C$_2$–C$_{12}$-alkenyl, —NHC(S)NH—C$_2$–C$_{12}$-alkenyl, —NHC(S)NH—C$_3$–C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$–C$_{12}$-alkyl, —NHC(NH)NH—C$_2$–C$_{12}$-alkenyl, —NHC(NH)NH—C$_2$–C$_{12}$-alkenyl, —NHC(NH)NH—C$_3$–C$_{12}$-cycloalkyl, —NHC(NH)NH-aryl, —NHC(NH)NH-heteroaryl, —NHC(NH)NH-heterocycloalkyl, NHC(NH)—C$_1$–C$_{12}$-alkyl, —NHC(NH)—C$_2$–C$_{12}$-alkenyl, —NHC(NH)—C$_2$–C$_{12}$-alkenyl, —NHC(NH)—C$_3$–C$_{12}$-cycloalkyl, —NHC(NH)-aryl, —NHC(NH)-heteroaryl, —NHC(NH)-heterocycloalkyl, —C(NH)NH—C$_1$–C$_{12}$-alkyl, —C(NH)NH—C$_2$–C$_{12}$-alkenyl, —C(NH)NH—C$_2$–C$_{12}$-alkenyl, —C(NH)NH—C$_3$–C$_{12}$-cycloalkyl, —C(NH)NH-aryl, —C(NH)NH-heteroalkyl, —C(NH)NH-heterocycloalkyl, —S(O)—C$_1$–C$_{12}$-alkyl, —S(O)—C$_2$–C$_{12}$-alkenyl, —S(O)—C$_2$–C$_{12}$-alkenyl, —S(O)—C$_1$–C$_{12}$-cycloalkyl, —S(O)-aryl, —S(O)-heteroaryl, —S(O)-heterocycloalkyl —SO$_2$NH$_2$, —SO$_2$NH—C$_1$–C$_{12}$-alkyl, —SO$_2$NH—C$_2$–C$_{12}$-alkenyl, —SO$_2$NH—C$_2$–C$_{12}$-alkenyl, —SO$_2$NH—C$_3$–C$_{12}$-cycloalkyl, —SO$_2$NH-aryl, —SO$_2$NH-heteroaryl, —SO$_2$NH-heterocycloalkyl, —NHSO$_2$—C$_1$–C$_{12}$-alkyl, —NHSO$_2$—C$_2$–C$_{12}$-alkenyl, —NHSO$_2$—C$_2$–C$_{12}$-alkenyl, —NHSO$_2$—C$_3$–C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$–C$_{12}$-cycloalkyl, -methoxymethoxy, -methoxyethoxy, —SH, —S—C$_1$–C$_{12}$-alkyl, —S—C$_2$–C$_{12}$-alkenyl, —S—C$_2$–C$_{12}$-alkenyl, —S—C$_3$–C$_{12}$-cycloalkyl, —S-aryl, —S-heteroaryl, —S-heterocycloalkyl, or methylthiomethyl.

The term "heteroarylalkyl," as used herein, refers to a C$_1$–C$_3$ alkyl or C$_1$–C$_6$ alkyl residue residue attached to a heteroaryl ring. Examples include, but are not limited to, pyridinylmethyl, pyrimidinylethyl and the like.

The term "substituted heteroarylalkyl," as used herein, refers to a heteroarylalkyl group, as previously defined, substituted by independent replacement or one, two, or three of the hydrogen atoms thereon with substituents including, but not limited to, —F, —Cl, —Br, —I, —OH, protected hydroxy, —NO$_2$, —CN, —C$_1$–C$_{12}$-alkyl optionally substituted with halogen, C$_2$–C$_{12}$-alkenyl optionally substituted with halogen, —C$_2$–C$_{12}$-alkynyl optionally substituted with halogen, —NH$_2$, protected amino, —NH—C$_1$–C$_{12}$-alkyl, —NH—C$_2$–C$_{12}$-alkenyl, —NH—C$_2$–C$_{12}$-alkenyl, —NH—C$_3$–C$_{12}$-cycloalkyl, —NH-aryl, —NH-heteroaryl, —NH-heterocycloalkyl, -dialkylamino, -diarylamino, -diheteroarylamino, —O—C$_1$–C$_{12}$-alkyl, —O—C$_2$–C$_{12}$-alkenyl, —O—C$_2$–C$_{12}$-alkenyl, —O—C$_3$–C$_{12}$-cycloalkyl, —O-aryl, —O-heteroaryl, —O-heterocycloalkyl, —C(O)—C$_1$–C$_{12}$-alkyl, —C(O)—C$_2$–C$_{12}$-alkenyl, —C(O)—C$_2$–C$_{12}$-alkenyl, —C(O)—C$_3$–C$_{12}$-cycloalkyl, —C(O)-aryl, —C(O)-heteroaryl, —C(O)-heterocycloalkyl, —CONH$_2$, —CONH—C$_1$–C$_{12}$-alkyl, —CONH—C$_2$–C$_{12}$-alkenyl, —CONH—C$_2$–C$_{12}$-alkenyl, —CONH—C$_3$–C$_{12}$-cycloalkyl, —CONH-aryl, —CONH-heteroaryl, —CONH-heterocycloalkyl, —OCO$_2$—C$_1$C$_{12}$-alkyl, —OCO$_2$—C$_2$–C$_{12}$-alkenyl, —OCO$_2$—C$_2$C$_{12}$-alkenyl, —OCO$_2$—C$_3$–C$_{12}$-cycloalkyl, —OCO$_2$-aryl, —OCO$_2$-heteroaryl, —OCO$_2$-heterocycloalkyl, —OCONH$_2$, —OCONH—C$_1$–C$_{12}$-alkyl, —OCONH—C$_2$–C$_{12}$-alkenyl, —OCONH—C$_2$–C$_{12}$-alkenyl, —OCONH—C$_3$–C$_{12}$-cycloalkyl, —OCONH-aryl, —OCONH-heteroaryl, —OCONH-heterocycloalkyl, —NHC(O)—C$_1$–C$_{12}$-alkyl, —NHC(O)—C$_2$–C$_{12}$-alkenyl, —NHC(O)—C$_2$–C$_{12}$-alkenyl, —NHC(O)—C$_3$–C$_{12}$-cycloalkyl, —NHC(O)-aryl, —NHC(O)-heteroaryl, —NHC(O)-heterocycloalkyl, —NHCO$_2$—C$_1$–C$_{12}$-alkyl, —NHCO$_2$—C$_2$–C$_{12}$-alkenyl, —NHCO$_2$—C$_2$–C$_{12}$-alkenyl, —NHCO$_2$—C$_3$–C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$–C$_{12}$-alkyl, —NHC(O)NH—C$_2$–C$_{12}$-alkenyl, —NHC(O)NH—C$_2$–C$_{12}$-alkenyl, —NHC(O)NH—C$_3$–C$_{12}$-cycloalkyl, —NHC(O)NH-aryl, —NHC(O)NH-heteroaryl, —NHC(O)NH-heterocycloalkyl, NHC(S)NH$_2$, NHC(S)NH—C$_1$–C$_{12}$-alkyl, —NHC(S)NH—C$_2$–C$_{12}$-alkenyl, —NHC(S)NH—C$_2$–C$_{12}$-alkenyl, —NHC(S)NH—C$_3$–C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$–C$_{12}$-alkyl, —NHC(NH)NH—C$_2$–C$_{12}$-alkenyl, —NHC(NH)NH—C$_2$–C$_{12}$-alkenyl, —NHC(NH)NH—C$_3$–C$_{12}$-cycloalkyl, —NHC(NH)NH-aryl, —NHC(NH)NH-heteroaryl, —NHC(NH)NH-heterocycloalkyl, NHC(NH)—C$_1$–C$_{12}$-alkyl, —NHC(NH)—C$_2$–C$_{12}$-alkenyl, —NHC(NH)—C$_2$–C$_{12}$-alkenyl, —NHC(NH)—C$_3$–C$_{12}$-cycloalkyl, —NHC(NH)-aryl, —NHC(NH)-heteroaryl, —NHC(NH)-heterocycloalkyl, —C(NH)NH—C$_1$–C$_{12}$-alkyl, —C(NH)NH—C$_2$–C$_{12}$-alkenyl, —C(NH)NH—C$_2$–C$_{12}$-alkenyl, —C(NH)NH—C$_3$–C$_{12}$-cycloalkyl, —C(NH)NH-aryl, —C(NH)NH-heteroaryl, —C(NH)NH-heterocycloalkyl, —S(O)—C$_1$–C$_{12}$-alkyl, —S(O)—C$_2$–C$_{12}$-alkenyl, —S(O)—C$_2$–C$_{12}$-alkenyl, —S(O)—C$_3$–C$_{12}$-cycloalkyl, —S(O)-aryl, —S(O)-heteroaryl, —S(O)-heterocycloalkyl —SO$_2$NH$_2$, —SO$_2$NH—C$_1$C$_{12}$-alkyl, —SO$_2$NH—C$_2$–C$_{12}$- alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$C$_{12}$-cycloalkyl, —S-aryl, —S-heteroaryl, —S-heterocycloalkyl, or methylthiomethyl.

The term "C$_1$-C$_6$ alkoxy," as used herein, refers to a C$_1$-C$_6$ alkyl group, as previously defined, attached to the parent molecular moiety through an oxygen atom. Examples of C$_1$-C$_6$-alkoxy include, but are not limited to, methoxy, ethoxy, propoxy, isopropoxy, n-butoxy, tert-butoxy, neopentoxy and n-hexoxy.

The term "C$_1$-C$_3$-alkyl-amino," as used herein, refers to one or two C$_1$-C$_3$-alkyl groups, as previously defined, attached to the parent molecular moiety through a nitrogen atom. Examples of C$_1$-C$_3$-alkyl-amino include, but are not limited to, methylamino, dimethylamino, ethylamino, diethylamino, and propylamino.

The term "alkylamino" refers to a group having the structure —NH(C$_1$-C$_{12}$ alkyl) where C$_1$-C$_{12}$ alkyl is as previously defined.

The term "dialkylamino" refers to a group having the structure —N(C$_1$-C$_{12}$ alkyl)(C$_1$-C$_{12}$ alkyl), where C$_1$-C$_{12}$ alkyl is as previously defined. Examples of dialkylamino are, but not limited to, dimethylamino, diethylamino, methylethylamino, piperidino, and the like.

The term "alkoxycarbonyl" represents an ester group, i.e., an alkoxy group, attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula —COOH.

The term "carboxamide," as used herein, refers to a group of formula —C(O)NH(C$_1$-C$_{12}$ alkyl) or —C(O)N(C$_1$-C$_{12}$ alkyl)(C$_1$-C$_{12}$ alkyl), —C(O)NH$_2$, and the like.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, *Protective Groups in Organic Synthesis*, 3$^{rd}$ edition, John Wiley & Sons, New York (1999). Examples of hydroxy protecting groups include, but are not limited to, methylthiomethyl, tert-butyl-dimethylsilyl, tert-butyldiphenylsilyl, acyl substituted with an aromatic group and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis*, 3$^{rd}$ edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4$^{th}$ ed., edited by John A. Riddick et al., Vol. II, in the *Techniques of Chemistry Series*, John Wiley & Sons, NY, 1986.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4$^{th}$ ed., edited by John A. Riddick et al., Vol. II, in the *Techniques of Chemistry Series*, John Wiley & Sons, NY, 1986.

"An effective amount," as used herein, refers to an amount of a compound which confers a therapeutic effect on the treated subject. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as I- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trance may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1–19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the an such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the compounds of this invention, including the compounds of formulae described herein, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

As used herein, unless otherwise indicated, the term "bacterial infection(s)" or "protozoa infections"; includes, but is not limited to, bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include, but are not limited to, the following: pneumonia, otitis media, □herefore, bronchitis, tonsillitis, and mastoiditis related to infection by *Streptococcus pneumoniae, Haemophilus influenzae, Moraxella catarrhalis, Staphylococcus aureus,* or Peptostreptococcus spp. Pseudomonas spp.; pharynigitis, rheumatic fever, and glomerulonephritis related to infection by *Streptococcus pyogenes,* Groups C and G streptococci,

*Clostridium diptheriae,* or *Actinobacillus haemolyticum;* respiratory tract infections related to infection by *Mycoplasma pneumoniae, Legionella pneumophila, Streptococcus pneumoniae, Haemophilus influenzae,* or *Chlamydia pneumoniae;* uncomplicated skin and soft tissue infections, abscesses and osteomyelitis, and puerperal fever related to infection by *Staphylococcus aureus,* coagulase-positive staphylococci (i.e., *S. epidermidis, S. homolyticus,* etc.), *S. pyogenes, S. agalactiae,* Streptococcal groups C–F (minute-colony streptococci), viridans streptococci, Corynebacterium spp., Clostridium spp., or *Bartonella henselae;* uncomplicated acute urinary tract infections related to infection by *S. saprophyticus* or Enterococcus spp.; urethritis and cervicitis; and sexually transmitted diseases related to infection by *Chlamydia trachomatis, Haemophilus ducreyi, Treponema pallidum, Ureaplasma urealyticum,* or *Nesseria gonorrheae;* toxin diseases related to infection by *S. aureus* (food poisoning and Toxic shock syndrome), or Groups A, S, and C streptococci; ulcers related to infection by *Helicobacter pylori;* systemic febrile syndromes related to infection by *Borrelia recurrentis;* Lyme disease related to infection by *Borrelia burgdorferi;* conjunctivitis, keratitis, and dacrocystitis related to infection by *C. trachomatis, N. gonorrhoeae, S. aureus, S. pneumoniae, S. pyogenes, H. influenzae,* or Listeria spp.; disseminated *Mycobacterium avium* complex (MAC) disease related to infection by *Mycobacterium avium,* or *Mycobacterium intracellulare*; gastroenteritis related to infection by *Campylobacter jejuni;* intestinal protozoa related to infection by Cryptosporidium spp. Odontogenic infection related to infection by viridans streptococci; persistent cough related to infection by *Bordetella pertussis;* gas gangrene related to infection by *Clostridium perfringens* or Bacteroides spp.; Skin infection by *S. aureus,* Propionibacterium acne; atherosclerosis related to infection by *Helicobacter pylori* or *Chlamydia pneumoniae*; or the like.

Bacterial infections and protozoa infections and disorders related to such infections that may be treated or prevented in animals include, but are not limited to, the following: bovine respiratory disease related to infection by *P. haemolytica., P. multocida, Mycoplasma bovis,* or Bordetella spp.; cow enteric disease related to infection by *E. coli* or protozoa (i.e., □herefore, cryptosporidia, etc.), dairy cow mastitis related to infection by *S. aureus, S. uberis, S. agalactiae, S. dysgalactiae,* Klebsiella spp., Corynebacterium, or Enterococcus spp.; swine respiratory disease related to infection by *A. pleuropneumoniac., P. multocida,* or Mycoplasma spp.; swine enteric disease related to infection by *E. coli, Lawsonia intracellularis,* Salmonella spp., or *Serpulina hyodyisinteriae;* cow footrot related to infection by Fusobacterium spp.; cow metritis related to infection by *E. coli;* cow hairy warts related to Infection by *Fusobacterium necrophorum* or *Bacteroides nodosus;* cow pink-eye related to infection by *Moraxella bovis,* cow premature abortion related to infection by protozoa (i.e. neosporium); urinary tract infection in dogs and cats related to infection by *E. coli;* skin and soft tissue infections in dogs and cats related to infection by *S. epidermidis, S. intermedius,* coagulase neg. Staphylococcus or *P. multocida;* and dental or mouth infections in dogs and cats related to infection by Alcaligenes spp., Bacteroides spp., Clostridium spp., Enterobacter spp., Eubacterium spp., Peptostreptococcus spp., Porphfyromonas spp., Campylobacter spp., Actinomyces spp., Erysipelothrix spp., Rhodococcus spp., Trypanosoma spp., Plas,odium spp., Babesia spp., Toxoplasma spp., Pneumocystis spp., Leishmania spp., and Trichomonas spp. Or Prevotella spp. Other bacterial infections and protozoa infections and disorders related to such infections that may be treated or prevented in accord with the method of the present invention are referred to in J. P. Sanford at al., "The Sanford Guide To Antimicrobial Therapy," 26th Edition, (Antimicrobial Therapy, Inc., 1996).

Antibacterial Activity

Susceptibility tests can be used to quantitatively measure the in vitro activity of an antimicrobial agent against a given bacterial isolate. Compounds were tested for in vitro antibacterial activity by a micro-dilution method. Minimal Inhibitory Concentration (MIC) was determined in 96 well microliter plates utilizing the appropriate Mueller Hinton Broth medium (CAMHB) for the observed bacterial isolates. Antimicrobial agents were serially diluted (2-fold) in DMSO to produce a concentration range from about 64 $\mu$g/ml to about 0.03 $\mu$g/ml. The diluted compounds (2 $\mu$l/well) were then transferred into sterile, uninoculated CAMHB (0.2 mL) by use of a 96 fixed tip-pipetting station. The inoculum for each bacterial strain was standardized to $5 \times 10^5$ CFU/mL by optical comparison to a 0.5 McFarland turbidity standard. The plates were inoculated with 10 $\mu$l/well of adjusted bacterial inoculum. The 96 well plates were covered and incubated at 35+/−2° C. for 24 hours in ambient air environment. Following incubation, plate wells were visually examined by Optical Density measurement for the presence of growth (turbidity). The lowest concentration of an antimicrobial agent at which no visible growth occurs was defined as the MIC. The compounds of the invention generally demonstrated an MIC in the range from about 64 $\mu$g/ml to about 0.03 $\mu$g/ml.

All in vitro testing follows the guidelines described in the Approved Standards M7-A4 protocol, published by the National Committee for Clinical Laboratory Standards (NCCLS).

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and I) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or other animals by administering to the patient a therapeutically effective amount of a compound of the invention, in such amounts and for such time as is necessary to achieve the desired result.

By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

The pharmaceutical compositions of this invention can be administered orally to fish by blending said pharmaceutical compositions into fish feed or said pharmaceutical compositions may be dissolved in water in which infected fish are placed, a method commonly referred to as a medicated bath. The dosage for the treatment of fish differs depending upon the purpose of administration (prevention or cure of disease) and type of administration, size and extent of infection of the fish to be treated. Generally, a dosage of 5–1000 mg, preferably 20–100 mg, per kg of body weight of fish may be administered per day, either at one time or divided into several times. It will be recognized that the above-specified dosage is only a general range which may be reduced or increased depending upon the age, body weight, condition of disease, etc. of the fish.

Unless otherwise defined, all technical and scientific terms used herein are accorded the meaning commonly known to one with ordinary skill in the art. All publications, patents, published patent applications, and other references mentioned herein are hereby incorporated by reference in their entirety Abbreviations Abbreviations which may be used in the descriptions of the schemes and the examples that follow are: Ac for acetyl; AIBN for 2,2-azobisisobutyronitrile; Bn for benzyl; Boc for t-butoxycarbonyl; $Bu_3SnH$ for tributyltin hydride; Bz for benzoyl; CDI for carbonyldiimidazole; dba for dibenzylidene acetone; dppb for diphenylphosphino butane; DBU for 1,8-diazabicyclo[5.4.0]undec-7-ene; DCC for 1,3-dicyclohexylcarbodiimide; DEAD for diethylazodicarboxylate; DIBAL-H for diisopropyl aluminum hydride; DIC for 1,3-diisopropylcarbodiimide; DIEA for diisopropylethylamine; DMAP for dimethylaminopyridine; DMF for dimethyl formamide; DMSO for dimethylsulfoxide; DPPA for diphenylphosphoryl azide; LAH for lithium aluminum hydride; EtOAc for ethyl acetate; KHMDS for potassium bis(trimethylsilyl)amide; LDA for lithium diisopropyl amide; MeOH for methanol; $Me_2S$ for dimethyl sulfide; MOM for methoxymethyl; OMs for mesylate; OTos for tosylate; $NaN(TMS)_2$ for sodium bis(trimethylsilyl)amide; NCS for N-chlorosuccinimide; NMMO for 4-methylmorpholine N-oxide; PCC for pyridinium chlorochromate; PDC for pyridinium dichromate; Ph for phenyl; POPd for dihydrogen dichlorobis(di-tert-butylphosphino) palladium(II); TFA for triethylamine; THF for tetrahydrofuran; TPP or $PPh_3$ for triphenylphosphine; TBS for tert-butyl dimethylsilyl; and TMS for trimethylsilyl.

Synthetic Methods

The compounds and processes of the present invention will be better understood in connection with the following synthetic schemes which are illustrative of the methods by which the compounds of the invention may be prepared. The groups A, B, W, X, Y, Z, $R_2'$, $R_4''$ and $R_{11}$ are as previously defined unless otherwise noted below.

Scheme I
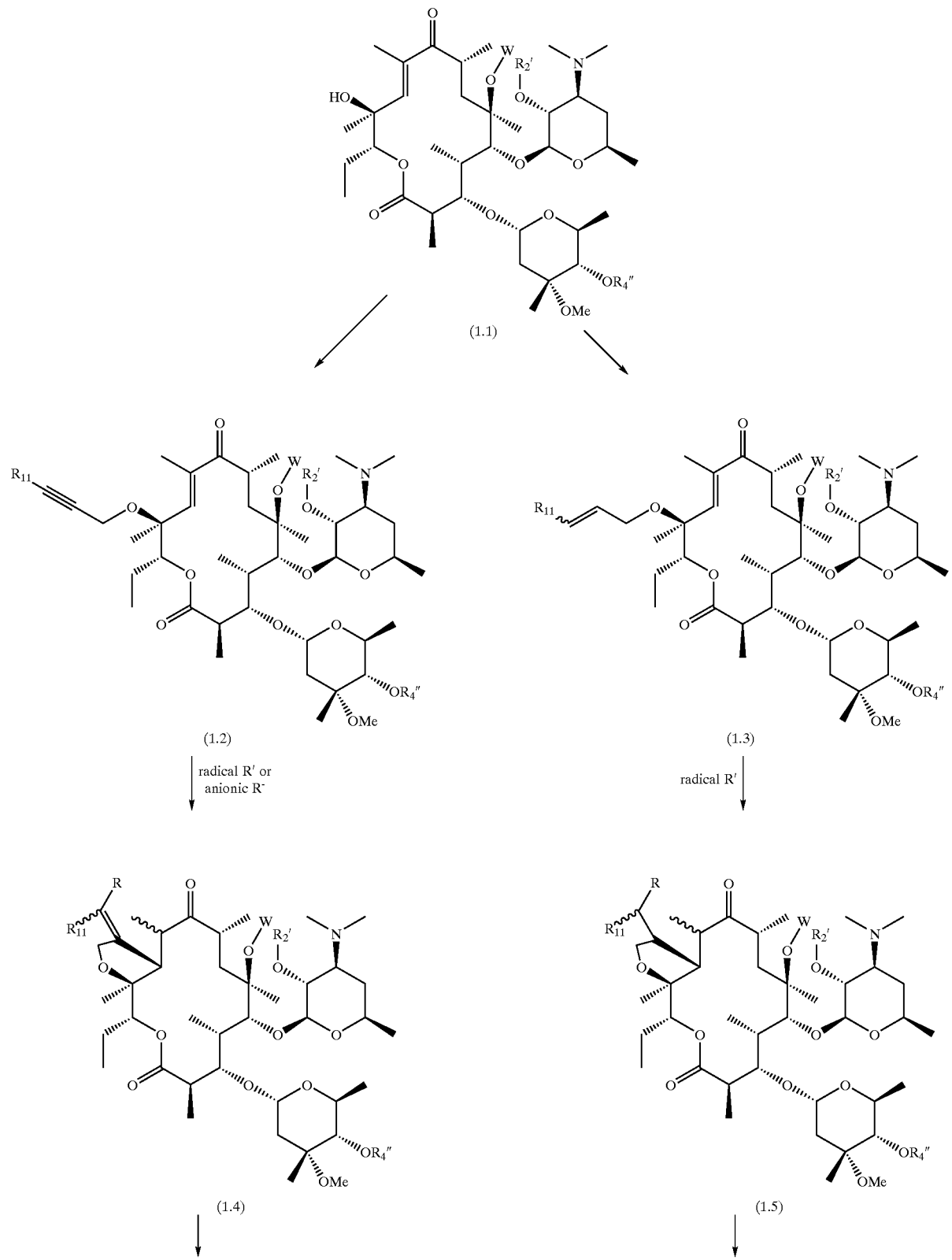

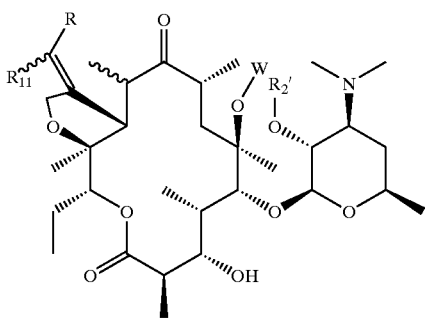

(1.6)

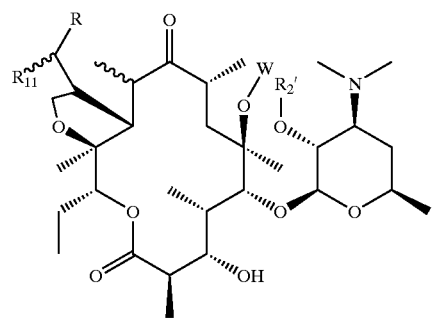

(1.7)

A process of the invention for the preparation of compounds of formula I, as illustrated in Scheme 1, involves preparing compounds of formula (1.4) and (1.5) by a tandem radical or anionic addition and cyclization of compounds of formula (1.2) or (1.3).

Intermediates (1.2) and (1.3) can be prepared by alkylation of the readily available compounds of formula (1.1) which can be prepared according to the process described by Baker et al. *J. Org. Chem.* 1988, 53, 2340–2345; Elliott et al. *J. Med. Chem.* 1988, 41, 1651–1659; Ma et al. *J. Med. Chem.* 2001, 44, 4137–4156, and Or et al. U.S. Pat. No. 6,075,011-B1. Typical alkylating conditions include treating compounds of formula (1.1) with a suitable alkylating agent, such as propargyl halide, allyl halide, allyl mesylate or the like, in the presence of a base such as $K_2CO_3$, NaOH, NaH, LDA or the like, optionally with a phase transfer catalyst such as tetrabutylammonium iodide, 18-crown-6 or the like, in THF, toluene, methylene chloride, DMF, DMSO, water or the like, or combinations thereof, at from about −50° C. to about 100° C. for 1 hour to 24 hours to provide compounds of formula (1.2) and (1.3). Alternatively, compounds of formula (1.3) can be obtained by reaction of a suitable alkylating agent such as tert-butyl allyl carbonate, tert-butyl 2-butenyl carbonate, allyl acetate, allyl benzoate or the like, in the presence of a palladium catalyst, such as palladium(II) acetate, tetrakis(triphenylphosphine)palladium(0), tris(dibenzylideneacetone)dipalladium(0), tetra(dibenzylidenacetone)dipalladium(0), palladium on carbon or the like, and a suitable phosphine ligand, such as triphenylphosphine, bis(diphenylphosphino)methane, 1,2-bis(diphenyl phosphino)ethane, 1,3-bis(diplienylphosphino)propane, 1,4-bis(diphenylphosphino)butane, tri-o-tolylphosphine, or the like, in an aprotic solvent, such as tetrahydrofuran, N,N-dimethylformamide, dimethylsulfoxide, N-methyl-2-pyrrolidinone, hexamethylphosphoric triamide, 1,2-dimethoxyethane, methyl-tert-butyl ether, heptane, acetonitrile, acetonitrile and ethyl acetate or the like, at from 40° C. to about 150° C. for 0.5 hour to about 48 hours.

In accordance with Scheme 1, compounds of formula I (1.4) and (1.5) of the present invention can be prepared by methods which are well known in the art involving a tandem radical addition and cyclization of intermediates (1.2) and (1.3) with a suitable radical species (R.) which can be generated from a radical precursor and an initiator. The radical R. can be centered as, but not limited to, carbon, silicon, tin, oxygen, sulfur, nitrogen, halogen with non-, mono-, di- or tri-substitution depending on the nature of the radical centered atom. A typical radical of this process is selected from, but not limited to, a group consisting of $PhCH_2·$, $Et_3Si·$, $(n-Bu)_3Sn·$, tert-BuO·, AcS·, $PhCH_2CH_2S·$ and Br·. A typical radical precursor for this process is selected from, but not limited to, $C_1$–$C_{12}$ alkyl halide, $C_2$–$C_6$ alkenyl halide, $C_2$–$C_6$ alkynyl halide, $C_2$–$C_6$ alkenyl tri($C_1$–$C_{12}$ alkyl)stannane, tri($C_1$–$C_{12}$ alkyl)stannane, hexamethyldistannane, trichlorosilane, triphenylsilane, tert-butyl hydrogen peroxide, thiolacetic acid, phenyl disulfide, N-bromosuccinamide and bromine. A typical radical initiator of this process can be selected from, but not limited to, a group consisting of AIBN, tert-butyl peroxide, benzoyl peroxide. The preferred radical reaction conditions of the present invention includes reacting the compounds of formula (1.2) or (1.3) with a radical generated from a group consisting of, but not limited to, halide, stannane, distannane, silane, mercaptan or disulfide, in the presence of AIBN, optionally in the presence of a reducing agent such as tributylstannane, diphenylsilane, sodium borohydride, magnesium, lithium aluminum hydride or the like, at 40° C. to 150° C. for a period of from 1 hour to 10 days, in an aprotic solvents, such as tetrahydrofuran, N,N-dimethylformamide, dimethyl sulfoxide, N-methyl-2-pyrrolidinone, 1,2-dimethioxyethane, methyl-tert-butyl ether, cyclohexane, heptane, acetonitrile, benzene, toluene and ethyl acetate or the like.

Alternatively compounds of formula I (1.4) of the present invention may be prepared by a tandem anionic addition and cyclization of intermediates (1.2) with a suitable anionic species ($R^−$) which can be generated from an organometallic precursor. Typically a compound of formula (1.2) is reacted with an organometallic reagents, such as allylmagnesium chloride, methylmagnesium iodide, phenyllithium, triethylaluminum, triethoxysilane, or the like, in the presence of 0–100% molar percent (relative to compound 1.2) of a transitional metal or its salt or its complex such as palladium, iridium, chromium(III) chloride, cerium(III) chloride, palladium(II) acetate, platinum(II) chloride, chloroplatinic acid, nonacahonyliron(0), titanocene(IV) dichloride, bis(1,5-cyclooctadiene)nickel(0), tetrakis(triphenylphosphine)palladium(0) or the like, at −78° C. to 100° C. for a period of from 0.5 to 48 hours, in an aprotic solvents, such as tetrahydrofuran, dimethyl sulfoxide, N-methyl-2-pyrrolidinone, 1,2-dimethoxyethane, methyl-tert-butyl ether, cyclohexane, heptane, acetonitrile, benzene and toluene or the like.

Another process of the invention involves the removal of the cladinose moiety of the compounds of formula I. The cladinose moiety of the macrolide compounds of formulae (1.4) and (1.5) can be removed to give compounds of formulae (1.6) and (1.7) in Scheme 1 by a dilute acid, such as hydrochloric acid, sulfuric acid, perchloric acid, nitric acid, chloroacetic acid, dichloroacetic acid, trifluoroacetic acid and p-toluenesulfonic acid or the like, in a suitable solvent, such as methanol, ethanol, isopropanol, butanol, water or the like, or the mixtures thereof, at 0° C. to about 80° C. for 0.5 hour to 24 hours.

When $R_2''$ is an acyl protecting group, it can be removed upon treatment with methanol at from room temperature to 60° C. When $R_2''$ is a silyl protecting group, the deprotection can be also effected by an acid, such as dilute hydrochloric acid, sulfuric acid, perchloric acid, nitric acid, chloroacetic acid, dichloroacetic acid, trifluoroacetic acid and p-toluenesulfonic acid or the like, or a fluoride, such as tetrabutylammonium fluoride, pyridinium fluoride, ammonium fluoride, hydrofluoric acid or the like, at from 0°C. to 50° C. for 0.5 to 24 hours.

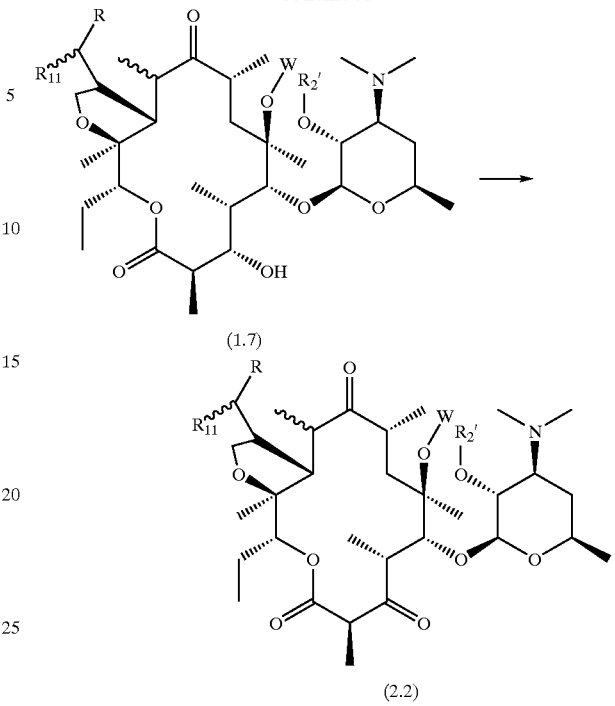

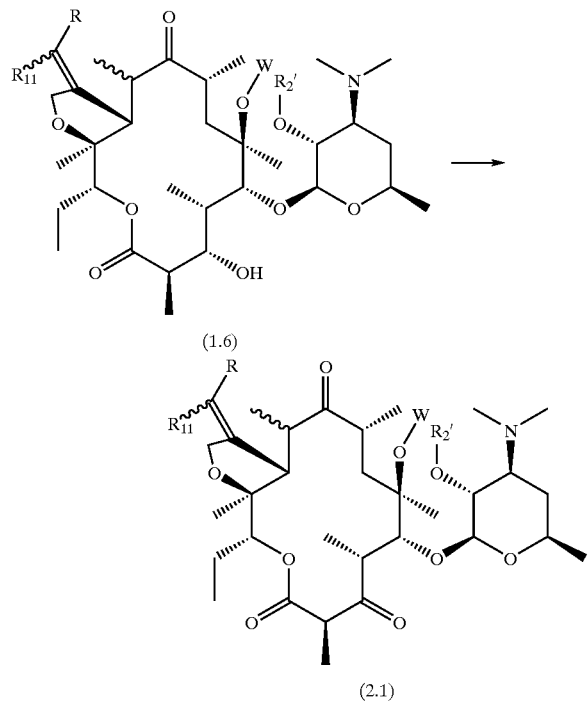

Compounds according to the invention (2.1) and (2.2) may be prepared by oxidation of the secondary alcohol using Dess-Martin periodinane as the oxidant. The reaction is typically run in an aprotic solvent at 0° to 25° C. for 0.5 to 12 hours.

Alternatively the oxidation can be accomplished using pyridinium chlorochromate, sulfur trioxide pyridine complex in dimethyl sulfoxide, tetra-n-propyl ammonium perruthenate and N-methyl morpholine N-oxide, Swern oxidation or the like. A more thorough discussion of the oxidation of secondary alcohols can be found in M. B. Smith and J. March "Advanced Organic Chemistry" $5^{th}$ ed., Wiley & Son, Inc, 2001, which is hereby incorporated by reference herein.

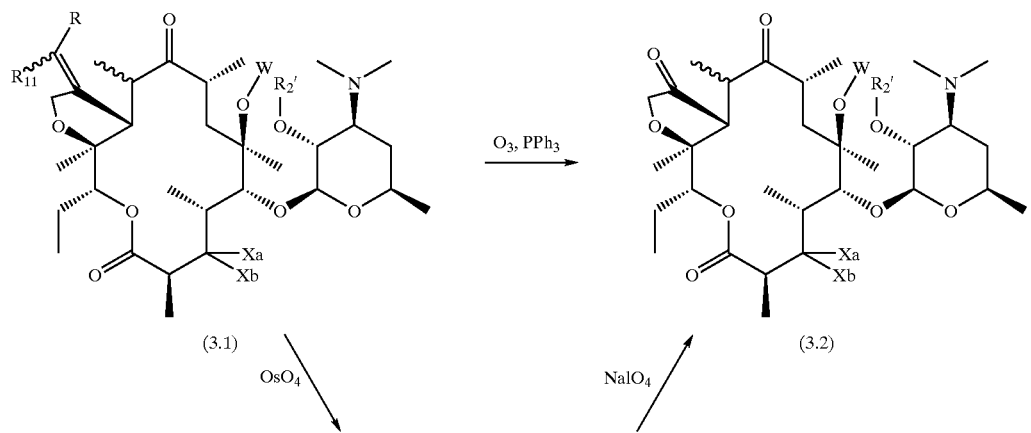

-continued

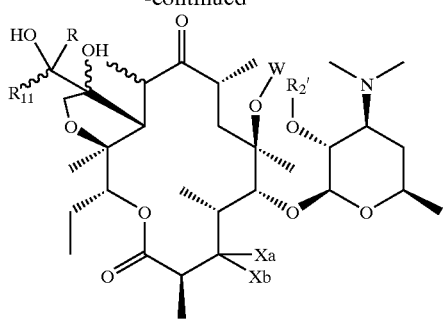

(3.3)

$X_a$ = OH, $X_b$ = H or $X_a$ and $X_b$ taken together with the carbon to which they are attached is C=O Conversion of the alkene of formula (3.1) into the ketone (3.2) can be accomplished by exposure of the alkene to ozone followed by decomposition of the ozonide intermediate with an appropriate reducing agent, as outlined in Scheme 3. The reaction is typically carried out in a solvent such as, for example, methanol, ethanol, ethyl acetate, glacial acetic acid, chloroform, methylene chloride or hexanes, or mixtures thereof, at from −78° C. to −20° C. Representative reducing agents include, for example, triphenylphosphine, trimethyl phosphite, thiourea, and dimethyl sulfide or the like. A more thorough discussion of ozonolysis and the conditions therefore can be found in M. B. Smith and J. March "Advanced Organic Chemistry" $5^{th}$ ed., Wiley & Son, Inc, 2001.

An alternative method for the preparation of the ketones (3.2) involves dihydroxylation of the alkene followed by diol cleavage. The glycol (3.3) is prepared by reacting the alkene (3.1), either with stoichiometric amounts of osmium tetrdoxide, or with catalytic amounts of osmium tetraoxide if an oxidant such as hydrogen peroxide, tert-butyl hydroperoxide, or N-methylmorpholine-N-oxide is present, in a variety of solvents such as 1,4-dioxane, tetrahydrofuran, tert-butanol, acetone, dimethyl ether, water or the like, or the mixture thereof, preferably at from 0° C. to 50° C.

The glycol (3.3) can be cleaved by a variety of reagents including, but not limited to, periodic acid, lead tetraacetate, manganese dioxide, potassium permanganate, sodium metaperiodate, and N-iodosuccinamide in a variety of solvents such as 1,4-dioxane, tetrahydrofuran, tert-butanol, acetone, ethanol, methanol, water or the like, or the mixture thereof, at from 0° C. to 50° C.

The synthesis of the ketone (3.2) can also be realized in one-pot by reacting the alkene (3.1) with either stoichiometric amounts or catalytic amounts of osmium tetraoxide and a glycol cleavage reagent, such as, for example, periodic acid, lead tetraacetate, manganese dioxide, potassium permanganate, sodium metaperiodate, and N-iodosuccinamide or the like, in a solvent such as 1,4-dioxane, tetrahydrofuran, tert-butanol, acetone, ethanol, methanol, water or the like, or mixtures thereof, at from 0° C. to 50° C.

Scheme 4

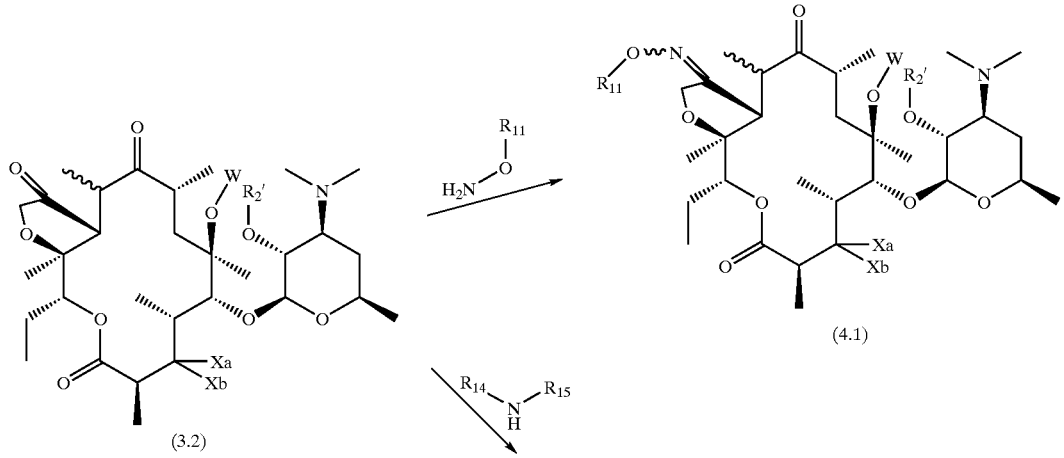

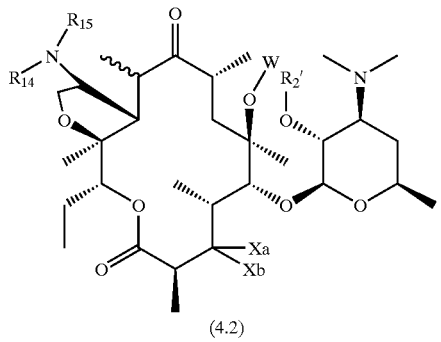

(4.2)

$X_a$ = OH, $X_b$ = H or $X_a$ and $X_b$ taken together with the carbon to which they are attached is C=O Compounds of formula (3.2) represent useful intermediates which can be further functionalized in a variety of ways. Scheme 4 details procedures for the conversion of the ketone (3.2) into an oxime of formula (4.1) or an amine of formula (4.2). The formation of oxime (4.1) can be accomplished under either acidic or basic conditions in a variety of solvents such as, for example, methanol, ethanol, water, tetrahydrofuran, 1,2-dimethoxyethane, ethyl acetate, or mixtures thereof, at from 0° C. to 70° C. over a period of 10 minutes to 12 hours. Representative acids include, but are not limited to, hydrochloric acid, phosphoric acid, sulfuric acid, p-toluenesulfonic acid, acetic acid and pyridinium p-toluenesulfonate. Bases which are useful are, for example, triethylamine, pyridine, diisopropylethyl amine, 2,6-lutidine, imidazole and potassium carbonate, and the like. The formation of amines (4.2) can be accomplished by reacting a ketone (3.2) with a primary or secondary amine and a suitable reducing agent such as, for example, hydrogen, sodium borohydride, sodium cyanoborohydride, LAH, zinc, DIBAL-H, triethylsilane, ammonium formate and the like, optionally in the presence of a catalyst such as Raney Ni, palladium on carbon, platinum dioxide, tetrakis(triphenylphosphine)palladium and the like in a suitable solvent such as methanol, acetonitrile, water, tetrahydrofuran, 1,2-dimethoxyethane, ethyl acetate, acetic acid, trifluoroacetic acid, hydrochloric acid or the like, or mixtures thereof, at a pH between 3 and 5 over a period of 5 minutes to 24 hours.

Scheme 5

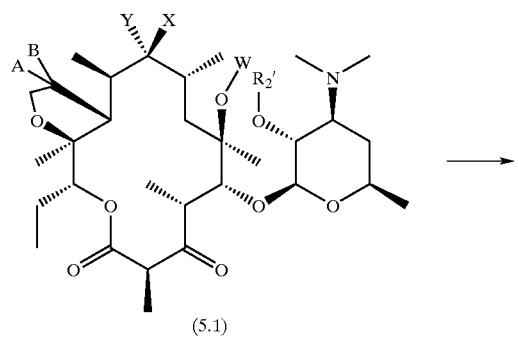

(5.1)

-continued

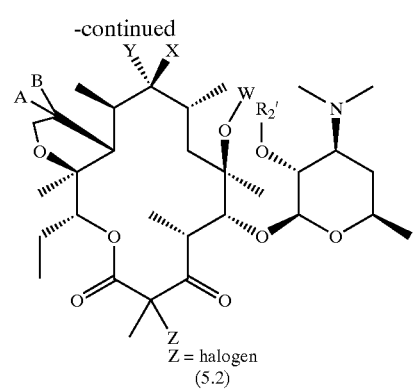

Z = halogen
(5.2)

Scheme 5 illustrates the procedure by which compounds of formula (5.1) may be converted to compounds of formula (5.2) by treatment with a halogenating reagent in a suitable solvent such as dimethylformamide, dimethyl sulfoxide, pyrrolidinone and the like. By the process disclosed in U.S. Pat. No. 6,124,269 and International Patent WO 00/62783, which are hereby incorporated by reference herein in their entirety. This reagent acts to replace a hydrogen atom with a halogen atom at the C-2 position of the ketolide. Various halogenating reagents may be suitable for this procedure.

Fluorinating reagents include, but are not limited to, N-fluorobenzenesulfonimide in the presence of base, 10% $F_2$ in formic acid, 3,5-dichloro-1-fluoropyridinium tetrafluoroborate, 3,5-dichloro-1-fluoropyridinium triflate, $(CF_3SO_2)_2NF$, N-fluoro-N-methyl-p-toluenesulfonamide in the presence of base, N-fluoropyridinium triflate, N-fluoroperfluoropiperidine in the presence of base. Chlorinating reagents include, but are not limited to, hexachloroethane in the presence of base, $CF_3CF_2CH_2ICl_2$, $SO_2Cl_2$, $SOCl_2$, $CF_3SO_2Cl$ in the presence of base, $Cl_2$, NaOCl in the presence of acetic acid. Brominating reagents include, but are not limited to, $Br_2$.pyridine.HBr, $Br_2$/acetic acid, N-bromosuccinimide in the presence of base, LDA/$BrCH_2CH_2Br$, or LDA/$CBr_4$. A suitable iodinating reagent is N-Iodosuccinimide in the presence of base, or $I_2$, for example. A preferred halogenating reagent is N-fluorobenzesulfonimide in the presence of sodium hydride.

Suitable bases for the halogenating reactions requiring them are compounds such as alkali metal hydrides, such as NaH and KH, or amine bases, such as LDA or triethylamine, for example. Different reagents may require different type of base, but this is well known within the art.

It will be appreciated by one skilled in the art that compounds of formula (5.2) can be substituted for compounds of formula (3.1) or (3.2) in the preceding examples if the corresponding C-2 halogenated product is desired.

EXAMPLES

The compounds and processes of the present invention will be described further in detail with respect to specific preferred embodiments by way of examples, it being understood that these are intended to be illustrative only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Compound of formula I: A and B taken together with the carbon atom to which they are attached are C=$CH_2$, L is $CH_2CH_3$ W is $CH_2CH$=$CH_2$, X and Y taken together with the carbon atom to which they are attached are C=O, Z is H, and $R_2'$ is H.

Step 1a. Compound 1.2 of Scheme I: W is $CH_2CH$=$CH_2$, $R_{11}$ is H, $R_2'$ is C(O)$CH_3$ and $R_4''$ is C(O)$CH_3$.

A mixture of 2',4"-bis-O-acetyl-6-O-allyl-11-deoxy-10, 11-didehydroerythromycin (640 mg, 0.76 mmol), tetrabutylammonium iodide (56 mg, 0.15 mmol), methylene chloride (4.0 mL), propargyl bromide (80% in toluene, 0.68 mL, 6.09 mmol) and sodium hydroxide (50% in water, 6.0 mL) was stirred at room temperature for 2 hours. The mixture was partitioned (ethtyl acetate and water). The organic phases were washed with water and brine, dried ($Na_2SO_4$) and evaporated. The residue was purified by chromatography (silica, hexanes:acetone/95:5 and 3:1) to give 258 mg (39%) of the title compound.

MS (ESI) m/z=878 (M+H)$^+$.

Step 1b. Compound 1.4 of Scheme 1: W is $CH_2CH$=$CH_2$, R and $R_{11}$ taken together with the carbon atom to which they are attached are CHSn$Bu_3$, $R_2'$ is C(O)$CH_3$ and $R_4''$ is C(O)$CH_3$.

A solution of the compound from Step 1a (250 mg, 0.28 mmol) in anhydrous benzene (5.7 mL) was heated to reflux with tributyltin hydride (249 mg, 0.85 mmol) in the presence of AIBN (11.5 mg) for 2 hours before evaporation. The residue was chromatographed (silica, hexanes:acetone/ 95:5~9:1) to give the title compound (163.5 mg, 49%).

MS (ESI) m/z=1168/1170 (M+H)$^+$.

Step 1c. Compound 1.6 of Scheme 1: R and $R_{11}$ taken together with the carbon atom to which they are attached are C=$CH_2$, W is $CH_2CH$=$CH_2$, and $R_2'$ is C(O)$CH_3$.

A solution of the compound from Step 1b (163.5 mg, 0.14 mmol) in ethanol (4.0 mL) was treated with hydrochloric acid (2 M, 4.0 mL) at 60° C. for 2 hours before partition (ethyl acetate and saturated NaHCO$_3$). The organic phases were washed with water and brine, dried ($Na_2SO_4$) and evaporated. The residue was purified by chromatography (silica, hexanes:acetone/95:5~4:1) to give the title compound (60.3 mg, 63%).

MS (ESI) m/z=680 (M+H)$^+$.

$^{13}$C NMR (125 MHz, CDCl$_3$): δ 215.7, 174.7, 145.8, 136.4, 116.3, 112.1, 100.1, 86.2, 81.1, 79.7, 77.6, 77.4, 71.6, 70.7, 68.8, 64.6, 63.5, 48.7, 45.4, 44.3, 40.6, 37.3, 36.5, 35.9, 31.3, 22.0, 21.1, 20.4, 19.5, 15.5, 15.3, 14.8, 10.5, 8.1.

Step 1d. Compound I: A and B taken together with the carbon atom to which they are attached are C=$CH_2$, L is $CH_2CH_3$, W is $CH_2CH$=$CH_2$, X and Y taken together with the carbon atom to which they are attached are C=O, Z is H, and $R_2'$ is C(O)$CH_3$ Into a solution of the compound from Step 1c (60.3 mg, 0.089 mmol) in dichloromethane (3.0 mL) was added Dess-Martin periodinane (56.4 mg, 0.13 mmol) at room temperature. The mixture was stirred at room temperature for 3.5 hours before additional Dess-Martin periodinane (60 mg, 0.14 mmol) was added. The solution was stirred at room temperature for another 1.5 hours and then partitioned with ethyl acetate and saturated sodium bicarbonate-saturated sodium thiosulfate (3:1). The organic phases were washed with water and brine, dried ($Na_2SO_4$) and evaporated before chromatography (silica, hexanes:acetone/95:5~85:15) to give the title compound (43.8 mg, 73%).

MS (ESI) m/z=678 (M+H)$^+$.

$^{13}$C NMR (125 MHz, CDCl$_3$): δ 215.4, 206.1, 169.9, 169.7, 145.4, 136.2, 116.4, 112.0, 100.3, 85.9, 78.8, 78.7, 75.1, 71.3, 70.5, 68.9, 64.3, 63.4, 50.6, 48.5, 45.1, 44.3, 40.6, 37.6, 36.1, 30.6, 22.1, 21.3, 21.0, 20.3, 19.5, 15.7, 14.8, 12.4, 10.5.

Step 1e. Compound I: A and B taken together with the carbon atom to which they are attached are C=$CH_2$, L is $CH_2CH_3$, W is $CH_2CH$=$CH_2$, X and Y taken together with the carbon atom to which they are attached are C=O, Z is H, and $R_2'$ is H.

A solution of the compound from Step 1d (6.5 mg) in methanol (2 mL) was refluxed for 2 hours and then evaporated to give the title compound (6.0 mg, 98%) as one of the C10 stereoisomers.

MS (ESI) m/z=636 (M+H)$^+$.

Example 2

Compound of formula I: A and B taken together with the carbon atom to which they are attached are C=$CH_2$, L is $CH_2CH_3$, W is $CH_2CH$=$CH_2$, X and Y taken together with the carbon atom to which they are attached are C=O, Z is H, and $R_2'$ is H.

Step 2a. Compound 1.6 of Scheme I: R and $R_{11}$ taken together with the carbon atom to which they are attached are C=$CH_2$, W is $CH_2CH$=$CH_2$, and $R_2'$ is C(O)$CH_3$.

A solution of the compound from Step 1b (163.5 mg, 0.14 mmol) in ethanol (4.0 mL) was treated with hydrochloric acid (2 M, 4.0 mL) at 60° C. for 2 hours before partition (ethyl acetate and saturated NaHCO$_3$). The organic phases were washed with water and brine, dried ($Na_2SO_4$) and evaporated. The residue was purified by chromatography (silica, hexanes:acetone/95:5~4:1) to give the title compound (24.9 mg, 26%).

MS (ESI) m/z=680 (M+H)$^+$.

$^{13}$C NMR (125 MHz, CDCl$_3$): δ 215.8, 176.7, 152.3, 136.3, 115.2, 107.6, 104.0, 92.2, 86.1, 80.8, 77.2, 72.1, 69.2, 64.7, 64.6, 61.8, 51.1, 48.4, 44.6, 40.8, 39.3, 38.1, 34.8, 29.7, 21.4, 21.2, 20.9, 19.8, 19.6, 15.4, 10.9, 10.7, 8.1.

Step 2b. Compound of formula I: A and B taken together with the carbon atom to which they are attached are C=$CH_2$, L is $CH_2CH_3$, W is $CH_2CH$=$CH_2$, X and Y taken together with the carbon atom to which they are attached are C=O, Z is H, and $R_2'$ is C(O)$CH_3$ Into a solution of the compound from Step 1c in dichloromethane is added Dess-Martin periodinane at room temperature. The mixture is stirred at room temperature for 3.5 hours before partition with ethyl acetate and saturated sodium bicarbonate-saturated sodium thiosulfate (3:1). The organic phases are washed with water and brine, dried ($Na_2SO_4$) and evaporated before chromatography to give the title compound as one of the C10 stereoisomers.

Step 2c. Compound of formula I: A and B taken together with the carbon atom to which they are attached are C=CH$_2$, L is CH$_2$CH$_3$, W is CH$_2$CH=CH$_2$, X and Y taken together with the carbon atom to which they are attached are C=O, Z is H, and R$_2$' is H.

A solution of the compound from Step 2b in methanol is refluxed for 2 hours and then evaporated to give the title compound as one of the C10 stereoisomers.

Example 3

Compound of formula I: A and B taken together with the carbon atom to which they are attached are C=CH$_2$, L is CH$_2$CH$_3$, W is CH$_2$CH=CH-(3-quinolyl), X and Y taken together with the carbon atom to which they are attached are C=O, Z is H, and R$_2$' is H.

Step 3a. Compound of formula I: A and B taken together with the carbon atom to which they are attached are C=CH$_2$, L is CH$_2$CH$_3$, W is CH$_2$CH=CH-(3-quinolyl), X and Y taken together with the carbon atom to which they are attached are C=O, Z is H, and R$_2$' is C(O)CH$_3$.

A mixture of the compound from Step 1d (30.0 mg, 0.044 mmol), tris(o-toluene)phosphine (10.0 mg, 0.033 mmol), palladium acetate (3.0 mg, 0.013 mmol), 3-bromoquinoline (0.015 mL, 0.11 mmol) and triethylamine (0.10 mL, 0.72 mmol) in acetonitrile (1.5 mL) was degassed and warmed to 70° C. The temperature was kept at 70° C. for 0.5 hour before being raised to 100° C. The mixture was kept at this temperature for 16 hours before being evaporated. The residue was further purified by chromatography (silica, hexanes:acetone/95:5~1.5:1) to give the title compound (12.7 mg, 36%).

MS (ESI) m/z=805 (M+H)$^+$.

Step 3b. Compound of formula I: A and B taken together with the carbon atom to which they are attached are C=CH$_2$, L is CH$_2$CH$_3$, W is CH$_2$CH=CH-(3-quinolyl), X and Y taken together with the carbon atom to which they are attached are C=O, Z is H, and R$_2$' is H.

A solution of the compound from Step 3a (12.7 mg) in methanol (2 mL) was refluxed for 2 hours and then evaporated. Chromatography (silica, CH$_2$CH$_2$:2M NH$_3$-MeOH/99:1~97:3) gave the title compound (8.0 mg, 67%).

MS (ESI) m/z=763 (M+H)$^+$.

Example 4

Compound of formula I: A and B taken together with the carbon atom to which they are attached are C=CH$_2$, L is CH$_2$CH$_3$, W is CH$_2$CH(O), X and Y taken together with the carbon atom to which they are attached are C=O, Z is H, and R$_2$' is H.

Step 4a. Compound 1.6 of Scheme 1: R and R$_{11}$ are each H, W is CH$_2$CH(O) and R$_2$' is C(O)CH$_3$.

To a solution of the compound of Step 1c of Example 1 in aqueous acetone at 25° C. is added OSO$_4$ (5 mol %) followed by NaIO$_4$ (4 equivalents) and the mixture is stirred for 4–6 hours. The reaction mixture is diluted with EtOAc and is washed with aqueous NaHCO$_3$, brine and dried over Na$_2$SO$_4$. Removal of the solvents in vacuo provides the title compound.

Step 4b. Compound of formula I: A and B taken together with the carbon atom to which they are attached are C=CH$_2$, L is CH$_2$CH$_3$, W is CH$_2$CH(O), X and Y taken together with the carbon atom to which they are attached are C=O, Z is H, and R$_2$' is C(O)CH$_3$.

The compound of Step 4a is treated according to the procedure of Step 1d of Example 1 to provide the title compound.

Step 4c. Compound of formula I: A and B taken together with the carbon atom to which they are attached are C=CH$_2$, L is CH$_2$CH$_3$, W is CH$_2$CH(O), X and Y taken together with the carbon atom to which they are attached are C=O, Z is H, and R$_2$' is H.

The compound of Step 4b is treated with methanol at 25° C. for 24 hours or at refluxing temperature for 24 hours. Removal of the solvent provides the title compound.

Example 5

Compound of formula I: A and B taken together with the carbon atom to which they are attached are C=CH$_2$, L is CH$_2$CH$_3$, W is CH$_2$C≡CH, X and Y taken together with the carbon atom to which they are attached are C=O, Z is H, and R$_2$' is H.

Step 5a. Compound of formula I: A and B taken together with the carbon atom to which they are attached are C=CH$_2$, L is CH$_2$CH$_3$, W is CH$_2$C≡CH, X and Y taken together with the carbon atom to which they are attached are C=O, Z is H, and R$_2$' is C(O)CH$_3$.

The compound of Step 4a is treated with an excess of phosphonium Wittig reagent according to the literature procedures ((a.). *Tetrahedron Lett.*, 1999, 40(49), 8575–8578. (b). *Synlett.*, 1996, (6), 521–522.) to provide the title compound.

Step 5b. Compound of formula I: A and B taken together with the carbon atom to which they are attached are C=CH$_2$, L is CH$_2$CH$_3$, W is CH$_2$C=CH, X and Y taken together with the carbon atom to which they are attached are C=O, Z is H, and R$_2$' is H.

The compound of Step 5a is treated with methanol at 25° C. for 24 hours or at refluxing temperature for 2–4 hours. Removal of the solvent provides the title compound.

Example 6

Compound of formula I: A and B taken together with the carbon atom to which they are attached are C=CH$_2$, L is CH$_2$CH$_3$, W is CH$_2$C≡C-(3-quinolyl), X and Y taken together with the carbon atom to which they are attached are C=O, Z is H and R$_2$' is H.

A mixture of a compound of Example 5 (1 equivalent) and Pd(PPh$_3$)$_2$Cl$_2$ (0.02 equivalents) in 5:1/acetonitrile:triethylamine is degassed and flushed with nitrogen, treated sequentially with CuI (0.01 equivalent) and 3-bromoquinoline (2–3 equivalents), stirred at room temperature for 10 minutes, heated at 70° C. for 6–24 hours, diluted with ethyl acetate and washed sequentially with water and brine and dried (Na$_2$SO$_4$). Removal of the solvents provides the title compound.

Example 7

Compound of formula I: A and B taken together with the carbon atom to which they are attached are C=CH$_2$, L is CH$_2$CH$_3$, W is CH$_2$CH$_2$NHCH$_2$-(4-chlorophenyl), X and Y taken together with the carbon atom to which they are attached are C=O, Z is H, and R$_2$' is H.

To a solution of the compound of Example 4 in methanol is added 4-chlorobenzylamine, excess NaBH$_3$CN and enough acetic acid to give a pH 4 at room temperature. The reaction mixture is stirred at room temperature for 4–8 hours. The mixture is cooled to 0° C., and neutralized with a solution of saturated aqueous Na$_2$CO$_3$ and extracted with CH$_2$Cl$_2$. The organic layer is dried over Na$_2$SO$_4$. Removal of the solvents and column chromatography on silica gel provides the title compound.

Example 8

Compound of formula I: A and B taken together with the carbon atom to which they are attached are C=CH$_2$, L is CH$_2$CH$_3$, W is CH$_2$C≡CH, X and Y taken together with the carbon atom to which they are attached are C=O, Z is F, and R$_2$' is H.

Step 8a. Compound of formula I: A and B taken together with the carbon atom to which they are attached are $C=CH_2$, L is $CH_2CH_3$, W is $CH_2C\equiv CH$, X and Y taken together with the carbon atom to which they are attached are $C=O$, Z is F, and $R_2'$ is $C(O)CH_3$.

A solution of the compound of Step 5a of Example 5 in DMF at 0° C. is treated with NaH (2 equivalents) and stirred at 0° C.-room temperature for 1 hour followed by addition of $(PhSO_2)_2NF$ (1 equivalent) at 0° C., and is stirred for 2 hours. The reaction mixture is taken up in ethyl acetate and is washed with water, $NaHCO_3$ and brine and dried over $Na_2SO_4$. Removal of the solvents provides the title compound.

Step 8b. Compound of formula I: A and B taken together with the carbon atom to which they are attached are $C=CH_2$, L is $CH_2CH_3$, W is $CH_2C\equiv CH$, X and Y taken together with the carbon atom to which they are attached are $C=O$, Z is F, and $R_2'$ is H.

The compound of Step 8a is treated with methanol at 25° C. for 24 hours or at refluxing temperature for 2–4 hours. Removal of the solvent provides the title compound.

Example 9

Compound of formula I: A and B taken together with the carbon atom to which they are attached are $C=CH_2$, L is $CH_2CH_3$, W is $CH_2\equiv C$-(3-quinolyl), X and Y taken together with the carbon atom to which they are attached are $C=O$, Z is F, and $R_2'$ is H.

A compound of Example 8 is treated according to the procedure of Example 6 to provide the title compound.

Examples 10 through 39 may be prepared according to the procedures described in Examples 3 through 9 and the synthetic schemes and discussions contained herein.

Example 10

Compound of formula I: A and B taken together with the carbon atom to which they are attached are $C=CH_2$, L is $CH_2CH_3$, W is $CH_2CH_2NCH_3CH_2$-phenyl, X and Y taken together with the carbon atom to which they are attached are $C=O$, Z is H, and $R_2'$ is H.

Example 11

Compound of formula I: A and B taken together with the carbon atom to which they are attached are $C=CH_2$, L is $CH_2CH_3$, W is $CH_2CH_2NCH_3CH_2$-(2-pyridyl), X and Y taken together with the carbon atom to which they are attached are $C=O$, Z is H, and $R_2'$ is H.

Example 12

Compound of formula I: A and 1 taken together with the carbon atom to which they are attached are $C=CH_2$, L is $CH_2CH_3$, W is $CH_2CH_2NCH_3CH_2$-(3-pyridyl), X and Y taken together with the carbon atom to which they are attached are $C=O$, Z is H, and $R_2'$ is H.

Example 13

Compound of formula I: A and B taken together with the carbon atom to which they are attached are $C=CH_2$, L is $CH_2CH_3$, W is $CH_2CH_2NCH_3CH_2$-(3quinolyl), X and Y taken together with the carbon atom to which they are attached are $C=O$, Z is H, and $R_2'$ is H.

Example 14

Compound of formula I: A and B taken together with the carbon atom to which they are attached are $C=CH_2$, L is $CH_2CH_3$, W is $CH_2CH_2NCH_3CH_2$-(2-pyridyl), X and Y taken together with the carbon atom to which they are attached are $C=O$, Z is F, and $R_2'$ is H.

Example 15

Compound of formula I: A and B taken together with the carbon atom to which they are attached are $C=CH_2$, L is $CH_2CH_3$, W is $CH_2CH_2NCH_3CH_2$-(3-quinolyl), X and Y taken together with the carbon atom to which they are attached are $C=O$, Z is F, and $R_2'$ is H.

Example 16

Compound or formula I: A and B taken together with the carbon atom to which they are attached are $C=CH_2$, L is $CH_2CH_3$, W is $CH_2CH=CH$-phenyl, X and Y taken together with the carbon atom to which they are attached are $C=O$, Z is H, and $R_2'$ is H.

Example 17

Compound of formula I: A and B taken together with the carbon atom to which they are attached are $C=CH_2$, L is $CH_2CH_3$, W is $CH_2CH=CH$-(2-pyridyl), X and Y taken together with the carbon atom to which they are attached are $C=O$, Z is H, and $R_2'$ is H.

Example 18

Compound of formula I: A and B taken together with the carbon atom to which they are attached are $C=CH_2$, L is $CH_2CH_3$, W is $CH_2CH=CH$-(3-pyridyl), X and Y taken together with the carbon atom to which they are attached are $C=O$, Z is H, and $R_2'$ is H.

Example 19

Compound of formula I: A and B taken together with the carbon atom to which they are attached are $C=CH_2$, L is $CH_2CH_3$, W is $CH_2CH=CH$-(3-(5-cyano)pyridyl), X and Y taken together with the carbon atom to which they are attached are $C=O$, Z is H, and $R_2'$ is H.

Example 20

Compound of formula I: A and B taken together with the carbon atom to which they are attached are $C=CH_2$, L is $CH_2CH_3$, W is $CH_2CH=CH$-(6-(aminocarbonyl)-3-quinolyl), X and Y taken together with the carbon atom to which they are attached are $C=O$, Z is H, and $R_2'$ is H.

Example 21

Compound of formula I: A and B taken together with the carbon atom to which they are attached are $C=CH_2$, L is $CH_2CH_3$, W is $CH_2CH=CH$-(3-quinolyl), X and Y taken together with the carbon atom to which they are attached are $C=O$, Z is F, and $R_2'$ is H.

Example 22

Compound of formula I: A and B taken together with the carbon atom to which they are attached are $C=CH_2$, L is $CH_2CH_3$, W is $CH_2CH=CH$-(3-pyridyl) X and Y taken together with the carbon atom to which they are attached are $C=O$, Z is F, and $R_2'$ is H.

Example 23

Compound of formula I: A and B taken together with the carbon atom to which they are attached are $C=CH_2$, L is $CH_2CH_3$, W is $CH_2C\equiv C$-phenyl, X and Y taken together with the carbon atom to which they are attached are $C=O$, Z is H, and $R_2'$ is H.

Example 24

Compound of formula I: A and B taken together with the carbon atom to which they are attached are $C=CH_2$, L, is $CH_2CH_3$, W is $CH_2C\equiv C$-(2-pyridyl), X and Y taken together with the carbon atom to which they are attached are $C=O$, Z is H, and $R_2'$ is H.

Example 25
Compound of formula I: A and B taken together with the carbon atom to which they are attached are C=CH$_2$, L is CH$_2$CH$_3$, W is CH$_2$C≡C-(3-pyridyl), X and Y taken together with the carbon atom to which they are attached are C=O, Z is H, and R$_2$' is H.

Example 26
Compound of formula I: A and B taken together with the carbon atom to which they are attached are C=CH$_2$, L is CH$_2$CH$_3$, W is CH$_2$C≡C-(3-(5-cyano)pyridyl), X and Y taken together with the carbon atom to which they are attached are C=O, Z is H, and R$_2$' is H.

Example 27
Compound of formula I: A and B taken together with the carbon atom to which they are attached are C=CH$_2$, L is CH$_2$CH$_3$, W is CH$_2$C≡C-(5-(2-pyridyl)-2-(thienyl), X and Y taken together with the carbon atom to which they are attached are C=O, Z is H, and R$_2$' is H.

Example 28
Compound of formula I: A and B taken together with the carbon atom to which they are attached are C=CH$_2$, L is CH$_2$CH$_3$, W is CH$_2$C≡C-(5-(3-pyridyl)-2-(pyrrolyl), X and Y taken together with the carbon atom to which they are attached are C=O, Z is H, and R$_2$' is H.

Example 29
Compound of formula I: A and B taken together with the carbon atom to which they are attached are C=CH$_2$, L is CH$_2$CH$_3$, W is CH$_2$C≡C-(2-pyrimidyl)-2-thienyl), X and Y taken together with the carbon atom to which they are attached are C=O, Z is H, and R$_2$' is H.

Example 30
Compound of formula I: A and B taken together with the carbon atom to which they are attached are C=CH$_2$, L is CH$_2$CH$_3$, W is CH$_2$C≡C-(5-(2-pyrazinyl)-2-pyrrolyl), X and Y taken together with the carbon atom to which they are attached are C=O, Z is H, and R$_2$' is H.

Example 31
Compound of formula I: A and B taken together with the carbon atom to which they are attached are C=CH$_2$, L is CH$_2$CH$_3$, W is CH$_2$C≡C-(6-quinolyl), X and Y taken together with the carbon atom to which they are attached are C=O, Z is H, and R$_2$' is H.

Example 32
Compound of formula I: A and B taken together with the carbon atom to which they are attached are C=CH$_2$, L is CH$_2$CH$_3$, W is CH$_2$C≡C-phenyl, X and Y taken together with the carbon atom to which they are attached are C=O, Z is F, and R$_2$' is H.

Example 33
Compound of formula I: A and B taken together with the carbon atom to which they are attached are C=CH$_2$, L is CH$_2$CH$_3$, W is CH$_2$C≡C-(2-pyridyl), X and Y taken together with the carbon atom to which they are attached are C=O, Z is F, and R$_2$' is H.

Example 34
Compound of formula I: A and B taken together with the carbon atom to which they are attached are C=CH$_2$, L is CH$_2$CH$_3$, W is CH$_2$C≡C-(3-pyridyl), X and Y taken together with the carbon atom to which they are attached are C=O, Z is H, and R$_2$' is H.

Example 35
Compound of formula I: A and B taken together with the carbon atom to which they are attached are C=CH$_2$, L is CH$_2$CH$_3$, W is CH$_2$C≡C-(3-(5-cyano)pyridyl), X and Y taken together with the carbon atom to which they are attached are C=O, Z is F, and R$_2$' is H.

Example 36
Compound of formula I: A and B taken together with the carbon atom to which they are attached are C=CH$_2$, L is CH$_2$CH$_3$, W is CH$_2$C≡C-(5-(2-pyridyl)-2-thienyl), X and Y taken together with the carbon atom to which they are attached are C=O, Z is F, and R$_2$' is H.

Example 37
Compound of formula I: A and B taken together with the carbon atom to which they are attached are C=CH$_2$, L is CH$_2$CH$_3$, W is CH$_2$C≡C-(5-(2-pyrimidyl)-2-thienyl), X and Y taken together with the carbon atom to which they are attached are C=O, Z is F, and R$_2$' is H.

Example 38
Compound of formula I: A and B taken together with the carbon atom to which they are attached are C=CH$_2$, L is CH$_2$CH$_3$, W is CH$_2$C≡C-(5-(2-pyridinyl)-2-pyrrolyl), X and Y taken together with the carbon atom to which they are attached are C=O, Z is F, and R$_2$' is H.

Example 39
Compound of formula I: A and B taken together with the carbon atom to which they are attached are C=CH$_2$, L is CH$_2$CH$_3$, W is CH$_2$C≡C-(5-(2-pyrazinyl)-2-pyrrolyl), X and Y taken together with the carbon atom to which they are attached are C=O, Z is F, and R$_2$' is H.

Although the invention has been described in detail with respect to various preferred embodiments it is not intended to be limited thereto, but rather those skilled in the art will recognize that variations and modifications may be made therein which are within the spirit of the invention and the scope of the appended claims.

What is claimed is:

1. A compound represented by the formula

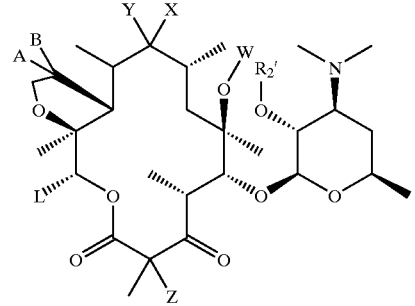

or a pharmaceutically acceptable salt, ester or prodrug thereof wherein
A is selected from:
  (a) —OH;
  (b) —OR$_p$, where R$_p$ is a hydroxy protecting group;
  (c) —R$_1$, where R$_1$ is selected from;
    1. aryl;
    2. substituted aryl;
    3. heteroaryl; and
    4. substituted heteroaryl;
  (d) —OR$_1$, where R$_1$ is as previously defined;

(e) —$R_2$, where $R_2$ is selected from;
  1. hydrogen;
  2. halogen;
  3. $C_1$–$C_6$ alkyl containing 0, 1, 2, or 3 heteroatoms selected from O, S and N, optionally substituted with one or more substituents selected from halogen, cyano, oxo, aryl, substituted aryl, heteroaryl and substituted heteroaryl;
  4. $C_2$–$C_6$ alkenyl containing 0, 1, 2, or 3 heteroatoms selected from O, S and N, optionally substituted with one or more substituents selected from halogen, cyano, oxo, aryl, substituted aryl, heteroaryl and substituted heteroaryl; and
  5. $C_2$–$C_6$ alkynyl containing 0, 1, 2, or 3 heteroatoms selected from O, S and N, optionally substituted with one or more substituents selected from halogen, cyano, oxo, aryl, substituted aryl, heteroaryl and substituted heteoraryl;
(f) —$OR_2$, where $R_2$ is previously defined;
(g) —$S(O)_2R_{11}$, where n=0, 1 or 2, and $R_{11}$ is selected from hydrogen, $R_1$ and $R_2$, where $R_1$ and $R_2$ are as previously defined;
(h) —$OC(O)R_{11}$, where $R_{11}$ is as previously defined;
(i) —$C(O)R_{11}$, where $R_{11}$ is as previously defined;
(j) —$C(O)NHR_{11}$, where $R_{11}$ is as previously defined;
(k) —$OC(O)NHR_{11}$, where $R_{11}$ is as previously defined;
(l) —$NHC(O)R_{11}$, where $R_{11}$ is as previously defined;
(m) —$NHC(O)NHR_{11}$, where $R_{11}$ is as previously defined;
(n) —$NHS(O)R_{11}$, where n and $R_{11}$ are as previously defined;
(o) —$NR_{14}R_{15}$, where $R_{14}$ and $R_{15}$ each independently $R_{11}$, where $R_{11}$ is as previously defined; and
(p) —$NH_3$, where $R_3$ is an amino protecting group;
B is selected from:
  (a) hydrogen;
  (b) deuterium;
  (c) —CN;
  (d) —$NO_2$;
  (e) halogen;
  (f) —OH;
  (g) —$R_1$, where $R_1$ is as previously defined;
  (h) —$R_2$, where $R_2$ is as previously defined; and
  (i) —$OR_p$, where $R_p$ is as previously defined;
provided that when B is halogen, —$NO_2$, —OH or $OR_p$, A is $R_1$ or $R_2$;
or, alternatively, A and B taken together with the carbon atom to which they are attached are selected from:
  (a) C=O;
  (b) $C(OR_2)_2$, where $R_2$ is as previously defined;
  (c) $C(SR_2)_2$, where $R_2$ is as previously defined;
  (d) $C(OR_{12})(OR_{13})$, where $R_{12}$ and $R_{13}$ taken together are —$(CH_2)_m$—, and where m is 2 or 3;
  (e) $C(SR_{12})(SR_{13})$, where $R_{12}$ and $R_{13}$ taken together are —$(CH_2)_m$—, where m is as previously defined;
  (f) C=$CR_{11}R_{14}$, where $R_{11}$ and $R_{14}$ are as previously defined;
  (g) C=N—O—$R_{11}$, where $R_{11}$ is as previously defined;
  (h) C=$NNHR_{11}$, where $R_{11}$ is as previously defined;
  (i) C=$NNHC(O)R_{11}$, where $R_{11}$ is as previously defined;
  (j) C=NN=$CR_{11}R_{14}$, where $R_{11}$ and $R_{14}$ are as previously defined;
  (k) C=$NNHC(O)NHR_{11}$, where $R_{11}$ is as previously defined;
  (l) C=$NNHS(O)_nR_{11}$, when n and $R_{11}$ are as previously defined;
  (m) C=$NNHR_3$, where $R_3$ is as previously defined; and
  (n) C=$NR_{11}$, where $R_{11}$ is as previously defined;
one of X and Y is hydrogen and the other is selected from:
  (a) hydrogen,
  (b) deuterium;
  (c) —OH;
  (d) —$OR_p$, where $R_p$ is as previously defined; and
  (e) —$NR_4R_5$, where $R_4$ and $R_5$ are each independently selected from:
    1. hydrogen; and
    2. $C_1$–$C_{12}$ alkyl, optionally substituted with one or more substituents selected from halogen, cyano, aryl, substituted aryl, heteroaryl and substituted heteroaryl; or $R_4$ and $R_5$, taken together with the nitrogen atom to which they are attached form a 3–10 membered heteroalkyl ring containing 0–2 additional hetero atoms selected from the group consisting of O, S and N; or
alternatively, X and Y taken together with the carbon atom to which they are attached are selected from:
  (a) C=O;
  (b) C=$NR_{11}$, where $R_{11}$ is as previously defined;
  (c) C=$NC(O)R_{11}$, where $R_{11}$ is as previously defined;
  (d) C=N—$OR_6$, where $R_4$ is selected from:
    1. hydrogen;
    2. —$CH_2O(CH_2)_2OCH_3$,
    3. —$CH_2O(CH_2O)_nCH_3$, where n is as previously defined;
    4. —$C_1$–$C_{12}$ alkyl, optionally substituted with one or more substituents selected from halogen, cyano, aryl, substituted aryl, heteroaryl and substituted heteroaryl;
    5. $C_3$–$C_{12}$ cycloalkyl;
    6. $C(O)$—$C_1$–$C_{12}$ alkyl;
    7. $C(O)$—$C_3$–$C_{12}$ cycloalkyl;
    8. $C(O)$—$R_1$, where $R_1$ is as previously defined; and
    9. —$Si(R_a)(R_b)(R_c)$, wherein $R_a$, $R_b$ and $R_c$ are each independently selected from $C_1$–$C_{12}$ alkyl, aryl and substituted aryl; and
  (e) C=N—O—$C(R_7)(R_8)$—O—$R_6$, where $R_6$ is previously defined, provided that $R_6$ is not $C(O)$—$C_1$–$C_{12}$ alkyl, $C(O)$—$C_3$–$C_{12}$ cycloalkyl, or $C(O)$—$R_1$; and $R_7$ and $R_8$ taken together with the carbon atom to which they at attached form a $C_3$–$C_{12}$ cycloalkyl group or each is independently selected from:
    1. hydrogen; and
    2. $C_1$–$C_{12}$ alkyl;

L is selected from:
- (a) —CH(OH)CH$_3$;
- (b) C$_1$–C$_6$ alkyl, optionally substituted with one or more substituents selected from halogen, cyano, aryl, substituted aryl, heteroaryl, and substituted heteroaryl;
- (c) C$_2$–C$_6$ alkenyl, optionally substituted with one or more substituents selected from halogen, cyano, aryl, substituted aryl, heteroaryl, and substituted heteroaryl; and
- (d) C$_2$–C$_6$ alkynyl, optionally substituted with one or more substituents selected from halogen, cyano, aryl, substituted aryl, heteroaryl, and substituted heteroaryl;

W is selected from:
- (a) C$_2$–C$_6$ alkyl containing 0, 1, 2, or 3 heteroatoms selected from O, S and N, optionally substituted with one or more substituents selected from halogen, cyano, oxo, aryl, substituted aryl, heteroaryl, and substituted heteroaryl;
- (b) C$_2$–C$_6$ alkenyl containing 0, 1, 2, or 3 heteroatoms selected from O, S and N, optionally substituted with one or more substituents selected from halogen, cyano, oxo, aryl, substituted aryl, heteroaryl, and substituted heteroaryl; and
- (c) C$_2$–C$_6$ alkynyl containing 0, 1, 2, or 3 heteroatoms selected from O, S and N, optionally substituted with one or more substituents selected from halogen, cyano, oxo, aryl, substituted aryl, heteroaryl, and substituted heteroaryl;

Z is selected from:
- (a) hydrogen;
- (b) halogen; and
- (c) C$_1$–C$_6$ alkyl, optionally substituted with one or more substituents selected from halogen, cyano, aryl, substituted aryl, heteroaryl and substituted heteroaryl; and R$_2$' is hydrogen or R$_p$, where R$_p$ is as previously defined.

2. A compound according to claim 1 wherein L is ethyl and A, B, W, X, Y, Z and R$_2$' are as defined in claim 1.

3. A compound according to claim 2 wherein X and Y taken together with the carbon atom to which they are attached are C=O.

4. A compound according to claim 1 which is selected from:

Compound of formula I: A and B taken together with the carbon atom to which they are attached are C=CH$_2$, L is CH$_2$CH$_3$, W is CH$_2$CH=CH$_2$, X and Y taken together with the carbon atom to which they are attached are C=O, Z is H, and R$_2$' is H;

Compound of formula I: A and B taken together with the carbon atom to which they are attached are C=CH$_2$, L is CH$_2$CH$_3$, W is CH$_2$CH=CH-(3-quinolyl), X and Y taken together with the carbon atom to which they are attached are C=O, Z is H, and R$_2$' is H;

Compound of formula I: A and B taken together with the carbon atom to which they are attached are C=CH$_2$, L is CH$_2$CH$_3$, W is CH$_2$CH(O), X and Y taken together with the carbon atom to which they are attached are C=O, Z is H, and R$_2$' is H;

Compound of formula I: A and B taken together with the carbon atom to which they are attached are C=CH$_2$, L is CH$_2$CH$_3$, W is CH$_2$C≡CH, X and Y taken together with the carbon atom to which they are attached are C=O, Z is H, and R$_2$' is H;

Compound of formula I: A and B taken together with the carbon atom to which they are attached are C=CH$_2$, L is CH$_2$CH$_3$, W is CH$_2$C≡C-(3-quinolyl), X and Y taken together with the carbon atom to which they are attached are C=O, Z is H, and R$_2$' is H;

Compound of formula I: A and B taken together with the carbon atom to which they are attached are C=CH$_2$, L is CH$_2$CH$_3$, W is CH$_2$CH$_2$NHCH$_2$-(4-chlorophenyl), X and Y taken together with the carbon atom to which they are attached are C=O, Z is H, and R$_2$' is H;

Compound of formula I: A and B taken together with the carbon atom to which they are attached are C=CH$_2$, L is CH$_2$CH$_3$, W is CH$_2$C≡CH, X and Y taken together with the carbon atom to which they are attached are C=O, Z is F, and R$_2$' is H;

Compound of formula I: A and B taken together with the carbon atom to which they are attached are C=CH$_2$, L is CH$_2$CH$_3$, W is CH$_2$C≡C-(3-quinolyl), X and Y taken together with the carbon atom to which they are attached are C=O, Z is H, and R$_2$' is H;

Compound of formula I: A and B taken together with the carbon atom to which they are attached are C=CH$_2$, L is CH$_2$CH$_3$, W is CH$_2$CH$_2$NCH$_3$CH$_2$-phenyl, X and Y taken together with the carbon atom to which they are attached are C=O, Z is H, and R$_2$' is H;

Compound of formula I: A and B taken together with the carbon atom to which they are attached are C=CH$_2$, L is CH$_3$CH$_3$, W is CH$_2$CH$_2$NCH$_3$CH$_2$-(2-pyridyl), X and Y taken together with the carbon atom to which they are attached are C=O, Z is H, and R$_2$' is H;

Compound of formula I: A and B taken together with the carbon atom to which they are attached are C=CH$_2$, L is CH$_2$CH$_3$, W is CH$_2$CH$_2$NCH$_3$CH$_2$-(3-pyridyl), X and Y taken together with the carbon atom to which they are attached are C=O, Z is H, and R$_2$' is H;

Compound of formula I: A and B taken together with the carbon atom to which they are attached are C=CH$_2$, L is CH$_2$CH$_3$, W is CH$_2$CH$_2$NCH$_3$CH$_2$-(3-quinolyl), X and Y taken together with the carbon atom to which they are attached are C=O, Z is H, and R$_2$' is H;

Compound of formula I: A and B taken together with the carbon atom to which they are attached are C=CH$_2$, L is CH$_2$CH$_3$, W is CH$_2$CH$_2$NCH$_3$CH$_2$-(2-pyridyl), X and Y taken together with the carbon atom to which they are attached are C=O, Z is F, and R$_2$' is H;

Compound of formula I: A and B taken together with the carbon atom to which they are attached are C=CH$_2$, L is CH$_2$CH$_3$, W is CH$_2$CH$_2$NCH$_3$CH$_2$-(3-quinolyl), X and Y taken together with the carbon atom to which they are attached are C=O, Z is H, and R$_2$' is H;

Compound of formula I: A and B taken together with the carbon atom to which they are attached are C=CH$_2$, L is CH$_2$CH$_3$, W is CH$_2$CH=CH-phenyl, X and Y taken together with the carbon atom to which they are attached are C=O, Z is H, and R$_2$' is H;

Compound of formula I: A and B taken together with the carbon atom to which they are attached are C=CH$_2$, L is CH$_2$CH$_3$, W is CH$_2$CH=CH-(2-pyridyl), X and Y taken together with the carbon atom to which they are attached are C=O, Z is H, and R$_2$' is H;

Compound of formula I: A and B taken together with the carbon atom to which they are attached are C=CH$_2$, L is $CH_2CH_3$, W is $CH_2CH=CH$-(3-pyridyl), X and Y taken together with the carbon atom to which they are attached are C=O, Z is H, and $R_2'$ is H;

Compound of formula I: A and B taken together with the carbon atom to which they are attached are $C=CH_2$, L is $CH_2CH_3$, W is $CH_2CH=CH$-(3-(5-cyano)pyridyl), X and Y taken together with the carbon atom to which they are attached are C=O, Z is H, and $R_2'$ is H;

Compound of formula I: A and B taken together with the carbon atom to which they are attached are $C=CH_2$, L is $CH_2CH_3$, W is $CH_2CH=CH$-(6-(aminocarbonyl)-3-quinolyl), X and Y taken together with the carbon atom to which they are attached are C=O, Z is H, and $R_2'$ is H;

Compound of formula I: A and B taken together with the carbon atom to which they are attached are $C=CH_2$, L is $CH_2CH_3$, W is $CH_2CH=CH$-(3-quinolyl), X and Y taken together with the carbon atom to which they are attached are C=O, Z is F, and $R_2'$ is H;

Compound of formula I: A and B taken together with the carbon atom to which they are attached are $C=CH_2$, L is $CH_2CH_3$, W is $CH_2CH=CH$-(3-pyridyl), X and Y taken together with the carbon atom to which they are attached are C=O, Z is F, and $R_2'$ is H;

Compound of formula I: A and B taken together with the carbon atom to which they are attached are $C=CH_2$, L is $CH_2CH_3$, W is $CH_2C\equiv CH$-phenyl), X and Y taken together with the carbon atom to which they are attached are C=O, Z is H, and $R_2'$ is H;

Compound of formula I: A and B taken together with the carbon atom to which they are attached are $C=CH_2$, L is $CH_2CH_3$, W is $CH_2C\equiv C$-(2-pyridyl), X and Y taken together with the carbon atom to which they are attached are C=O, Z is H, and $R_2'$ is H;

Compound of formula I: A and B taken together with the carbon atom to which they are attached are $C=CH_2$, L is $CH_2CH_3$, W is $CH_2CH=C$-(3-pyridyl), X and Y taken together with the carbon atom to which they are attached are C=O, Z is H, and $R_2'$ is H;

Compound of formula I: A and B taken together with the carbon atom to which they are attached are $C=CH_2$, L is $CH_2CH_3$, W is $CH_2C=C$-(3-(5-cyano)pyridyl), X and Y taken together with the carbon atom to which they are attached are C=O, Z is H, and $R_2'$ is H;

Compound of formula I: A and B taken together with the carbon atom to which they are attached are $C=CH_2$, L is $CH_2CH_3$, W is $CH_2C=C$-(5-(2-pyridyl)-2-thienyl), X and Y taken together with the carbon atom to which they are attached are C=O, Z is H, and $R_2'$ is H;

Compound of formula I: A and B taken together with the carbon atom to which they are attached are $C=CH_2$, L is $CH_2CH_3$, W is $CH_2C=C$-(5-(3-pyridinyl)-2-pyrrolyl), X and Y taken together with the carbon atom to which they are attached are C=O, Z is H, and $R_2'$ is H;

Compound of formula I: A and B taken together with the carbon atom to which they are attached are $C=CH_2$, L is $CH_2CH_3$, W is $CH_2C=C$-(2-pyrimidyl)-2-thienyl), X and Y taken together with the carbon atom to which they are attached are C=O, Z is H, and $R_2'$ is H;

Compound of formula I: A and B taken together with the carbon atom to which they are attached are $C=CH_2$, L is $CH_2CH_3$, W is $CH_2C=C$-(5-(2-pyridyl)-2-pyrrolyl), X and Y taken together with the carbon atom to which they are attached are C=O, Z is H, and $R_2'$ is H;

Compound of formula I: A and B taken together with the carbon atom to which they are attached are $C=CH_2$, L is $CH_2CH_3$, W is $CH_2CH=C$-(6-quinoyl), X and Y taken together with the carbon atom to which they are attached are C=O, Z is H, and $R_2'$ is H;

Compound of formula I: A and B taken together with the carbon atom to which they are attached are $C=CH_2$, L is $CH_2CH_3$, W is $CH_2C=C$-phenyl, X and Y taken together with the carbon atom to which they are attached are C=O, Z is F, and $R_2'$ is H;

Compound of formula I: A and B taken together with the carbon atom to which they are attached are $C=CH_2$, L is $CH_2CH_3$, W is $C_2CH\equiv C$-(2-pyridyl), X and Y taken together with the carbon atom to which they are attached are C=O, Z is F, and $R_2'$ is H;

Compound of formula I: A and B taken together with the carbon atom to which they are attached are $C=CH_2$, L is $CH_2CH_3$, W is $C_2CH\equiv C$-(3-pyridyl), X and Y taken together with the carbon atom to which they are attached are C=O, Z is F, and $R_2'$ is H;

Compound of formula I: A and B taken together with the carbon atom to which they are attached are $C=CH_2$, L is $CH_2CH_3$, W is $CH_2C=C$-(3-(5-cyano)pyridyl), X and Y taken together with the carbon atom to which they are attached are C=O, Z is F, and $R_2'$ is H;

Compound of formula I: A and B taken together with the carbon atom to which they are attached are $C=CH_2$, L is $CH_2CH_3$, W is $CH_2C\equiv C$-(5-(2-pyridyl)-2-thienyl), X and Y taken together with the carbon atom to which they are attached are C=O, Z is F, and $R_2'$ is H;

Compound of formula I: A and B taken together with the carbon atom to which they are attached are $C=CH_2$, L is $CH_2CH_3$, W is $CH_2C\equiv C$-(5-(2-pyrimidyl)-2-thienyl), X and Y taken together with the carbon atom to which they are attached are C=O, Z is F, and $R_2'$ is H;

Compound of formula I: A and B taken together with the carbon atom to which they are attached are $C=CH_2$, L is $CH_2CH_3$, W is $CH_2C\equiv C$-(5-(2-pyridinyl)-2-pyrrolyl), X and Y taken together with the carbon atom to which they are attached are C=O, Z is F, and $R_2'$ is H; and Compound of formula I: A and B taken together with the carbon atom to which they are attached are $C=CH_2$, L is $CH_2CH_3$, W is $CH_2C=C$-(5-(2-pyrazinyl)-2-pyrrolyl), X and Y taken together with the carbon atom to which they are attached are C=O, Z is F, and $R_2'$ is H.

5. A pharmaceutical composition comprising a therapeutically effective amount of a compound of claim 1, or a pharmaceutically-acceptable salt, ester or prodrug thereof, in combination with a pharmaceutically acceptable carrier.

6. A method for controlling a bacterial infection in a subject comprising administering to a subject a therapeutically-effective amount of a pharmaceutically composition according to claim 5.

7. A method for the preparation of a compound of Formula I as defined in claim 1 wherein A and B taken together with the carbon atom to which they are attached are $C=CR_{11}R_1$ comprising the steps of:

i) reacting a compound represented by the formula

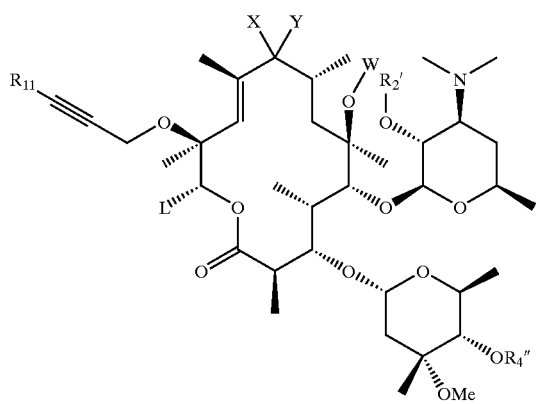

where L, W, X, Y, $R_2'$, $R_{11}$, and $R_4''$ are as defined in claim 1, with a radical species in the presence of 2,2'-azobisisobutyronitrile, optionally in the presence of a reducing agent in an aprotic solvent at from about 40° C. to about 150° C. for from 1 hour to 10 days to provide a compound of the formula

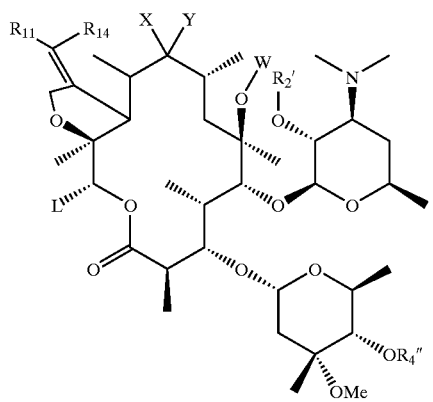

where L, W, X, Y, $R_2'$, $R_4''$, $R_{11}$ and $R_{14}$ are as defined in claim 1;

ii) reacting a compound of step (a) with an acidic solution at from room temperature to 100° C. to provide a compound of the formula

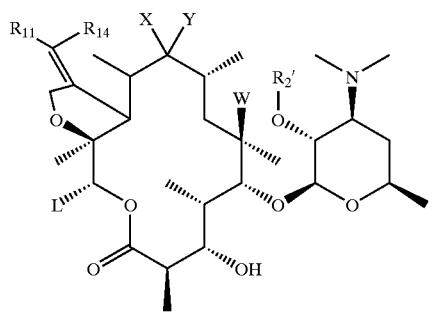

where, L, W, X, Y, $R_2'$, $R_{11}$ and $R_{14}$ are as defined claim 1, iii) oxidizing a compound of step (b) with an oxidizing agent to provide a compound of Formula I, wherein A and B taken together with the carbon atom to which they are attached are C=$CR_{11}R_{14}$, and where L, W, X, Y, Z, $R_2'$, $R_{11}$ and $R_{14}$ are as defined in claim 1.

8. A method for preparing a compound of formula I, as defined in claim 1, where A is hydrogen, B is —$CHR_{11}R_{14}$, comprising the steps of:

i) reacting a compound represented by the formula

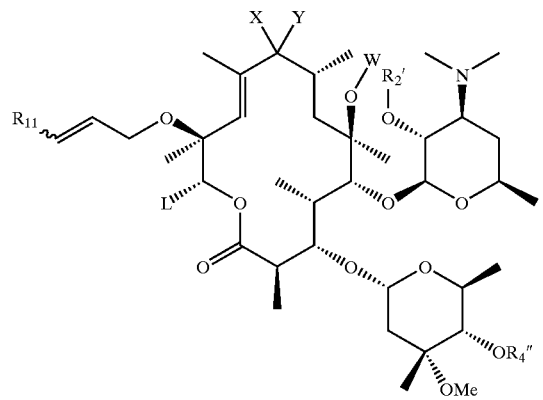

where L, W, X, Y, $R_2'$, $R_4''$, and $R_{11}$ are as defined in claim 1, with a radical species in the presence of 2,2'-azobisisobutyronitrile, optionally in the presence of a reducing agent in an aprotic solvent at from about 40° C. to about 150° C. for from 1 hour to 10 days to provide a compound of formula

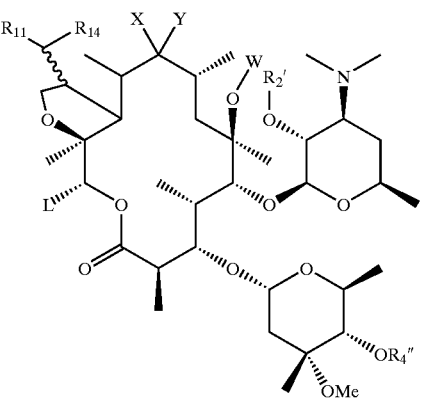

where L, W, X, Y, $R_2'$, $R_4''$, $R_{11}$ and $R_{14}$ are as defined in claim 1, ii) reacting a compound of step (a) with an acidic solution at from room temperature to 100° C. to provide a compound of the formula

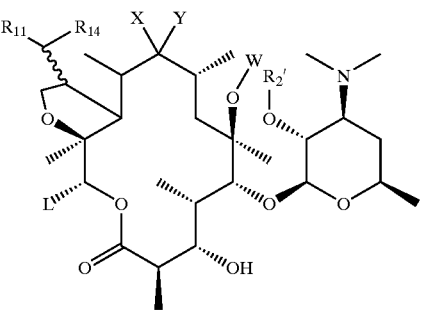

where L, W, X, Y, $R_2'$, $R_{11}$ and $R_{14}$ are as defined in claim 1, ii) oxidizing a compound of step (b) with an oxidizing agent to provide a compound of Formula I, wherein A is hydrogen, B is —$CHR_{11}R_{14}$, and where L, W, X, Y, $R_2'$, $R_{11}$ and $R_{14}$ are as defined in claim 1.

* * * * *

UNITED STATES PATENT AND TRADEMARK OFFICE
CERTIFICATE OF CORRECTION

PATENT NO.    : 6,774,115 B1
DATED         : August 10, 2004
INVENTOR(S)   : Yao-Ling Qiu, Ly Tam Phan and Yat Sun Or It is certified that error appears in the above-identified patent and that said Letters Patent is hereby corrected as shown below:

Column 47,
Line 20, delete "S(O)$_2$" and insert -- S(O)$_n$ --;
Line 35, delete "NHS(O)R$_{11}$" and insert -- NHS(O)$_n$R$_{11}$ --;
Line 37, after "R$_{15}$", insert -- are --.

Column 48,
Line 10, delete "when" and insert -- where --;
Line 41, delete "R$_4$" and insert -- R$_6$ --;
Line 64, delete "at" and insert -- are --.

Column 50,
Line 21, delete "H" and insert -- F --;
Line 30, delete "CH$_3$Ch$_3$" and insert -- CH$_2$CH$_3$ --;
Line 54, delete "H" and insert -- F --.

Column 51,
Lines 39, 45, 50, 56, 61 and 67, delete "C=C" and insert -- C≡C --;
Line 39, delete "CH=C" and insert -- CH≡C --;

Column 52,
Lines 11, 28 and 51, delete "CH=C" and insert -- CH≡C --;
Lines 11, 28 and 51, delete "C=C" and insert -- C≡C --;
Lines 17 and 22, delete "C$_2$CH=C-" and insert -- CH$_2$C≡C- --;
Line 67, delete "CR$_{11}$R$_1$" and insert -- CR$_{11}$R$_{14}$ --.

Column 53,
Line 2, delete " 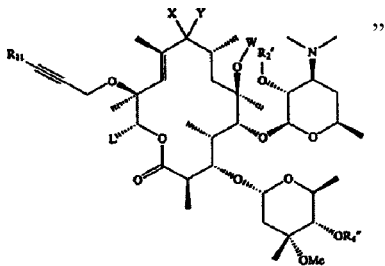 "

and insert -- 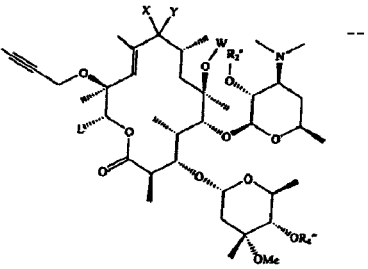 --

UNITED STATES PATENT AND TRADEMARK OFFICE
CERTIFICATE OF CORRECTION

PATENT NO. : 6,774,115 B1
DATED : August 10, 2004
INVENTOR(S) : Yao-Ling Qiu, Ly Tam Phan and Yat Sun Or It is certified that error appears in the above-identified patent and that said Letters Patent is hereby corrected as shown below:

Column 55,
Line 3, delete "ii" and insert -- iii --.

Column 56,
Line 1, after "Y," insert -- Z, --.

Signed and Sealed this

Fifteenth Day of March, 2005

JON W. DUDAS
*Director of the United States Patent and Trademark Office*